(12) United States Patent
Boukhayma et al.

(10) Patent No.: US 11,864,877 B2
(45) Date of Patent: *Jan. 9, 2024

(54) HEALTH MONITORING DEVICE INCLUDING PINNED PHOTODIODE

(71) Applicant: ECOLE POLYTECHNIQUE FÉDÉRALE DE LAUSANNE (EPFL), Lausanne (CH)

(72) Inventors: Assim Boukhayma, Neuchatel (CH); Antonino Caizzone, Milvignes (CH); Christian Enz, Saint-Aubin-Sauges (CH)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/149,690

(22) Filed: Jan. 4, 2023

(65) Prior Publication Data

US 2023/0157560 A1 May 25, 2023

Related U.S. Application Data

(63) Continuation of application No. 16/631,642, filed as application No. PCT/EP2018/069358 on Jul. 17, 2018, now Pat. No. 11,612,330.

(30) Foreign Application Priority Data

Jul. 21, 2017 (WO) .................. PCT/EP2017/068502

(51) Int. Cl.
*A61B 5/024* (2006.01)
*H01L 27/14* (2006.01)
*H04N 25/00* (2023.01)

(52) U.S. Cl.
CPC .......... *A61B 5/02427* (2013.01); *H01L 27/14* (2013.01); *H04N 25/00* (2023.01)

(58) Field of Classification Search
CPC ........ A61B 5/02427; A61B 2560/0247; A61B 2562/0233; A61B 2562/046;
(Continued)

(56) References Cited

U.S. PATENT DOCUMENTS

| 9,686,485 B2 * | 6/2017 | Agranov ................. H04N 25/70 |
| 11,612,330 B2 * | 3/2023 | Boukhayma ......... A61B 5/7203 257/431 |

(Continued)

FOREIGN PATENT DOCUMENTS

| JP | 2001036128 A | 2/2001 |
| JP | 2013104839 A | 5/2013 |

(Continued)

OTHER PUBLICATIONS

International Search Report and Written Opinion of the International Searching Authority, dated Sep. 17, 2018, from International Application No. PCT/EP2018/069358, filed on Jul. 17, 2018. 13 pages.

(Continued)

*Primary Examiner* — John P. Dulka
(74) *Attorney, Agent, or Firm* — HoustonHogle LLP

(57) ABSTRACT

The invention relates to a photoplethysmography (PPG) sensing device comprising—a pulsed light source, —at least one pixel to create photo-generated electrons, synchronized with said pulsed light source. It is mainly characterized in that each pixel comprises: —a pinned photodiode (PPD) having two electronic connection nodes, —a sense node (SN), to convert the photo-generated electrons into a voltage, and—a Transfer Gate (TGtransfer) transistor, having its source electronically connected to one electronic connection (Continued)

Figure 1:
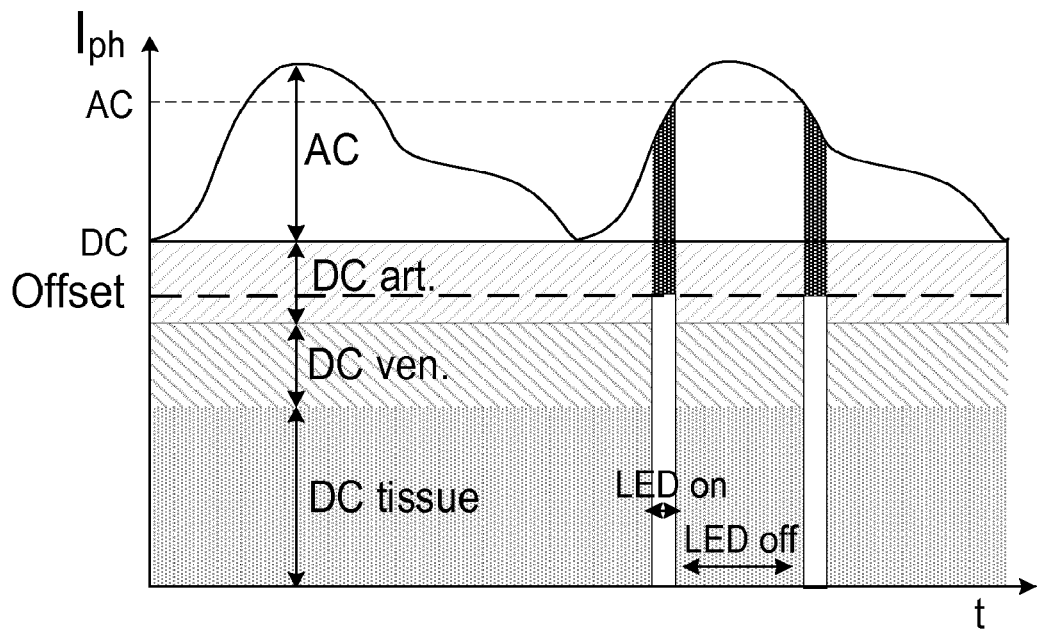

node of said pinned photodiode (PPD), and being configured to act as a transfer gate (TG) between said pinned photodiode (PPD) and said sense node (SN), allowing the photo-generated electrons to sink when the light is pulsed-off, the photo-generated electrons integration when the light is pulsed-on and the transfer of at least part of the integrated photo-generated electrons to said sense node for a read-out.

16 Claims, 16 Drawing Sheets

(58) Field of Classification Search
CPC . A61B 2562/12; A61B 5/7225; A61B 5/0295; A61B 5/14552; A61B 5/7246; A61B 5/7203; H01L 27/14; H01L 27/14612; H04N 25/00; H04N 25/46; H04N 25/50; H04N 25/77
See application file for complete search history.

(56) References Cited

U.S. PATENT DOCUMENTS

| | | |
|---|---|---|
| 2006/0146158 A1 | 7/2006 | Toros et al. |
| 2009/0090844 A1 | 4/2009 | Yan et al. |
| 2009/0207284 A1 | 8/2009 | Johnson |
| 2012/0056079 A1 | 3/2012 | Levine et al. |
| 2012/0056080 A1 | 3/2012 | Levine et al. |
| 2012/0193516 A1 | 8/2012 | Bogaerts |
| 2012/0193743 A1 | 8/2012 | Kawahito et al. |
| 2015/0076323 A1 | 3/2015 | Mabuchi |
| 2016/0183813 A1* | 6/2016 | Naima ................. A61B 5/0537 600/479 |
| 2017/0007138 A1 | 1/2017 | Kim et al. |
| 2017/0127988 A1 | 5/2017 | Tao et al. |
| 2017/0231500 A1 | 8/2017 | Rothberg et al. |

FOREIGN PATENT DOCUMENTS

| | | |
|---|---|---|
| JP | 2013211615 A | 10/2013 |
| JP | 2014060631 A | 4/2014 |
| JP | 2017018569 A | 1/2017 |
| WO | WO 2011/043339 | 4/2011 |

OTHER PUBLICATIONS

International Preliminary Report on Patentability, dated Jan. 30, 2020, from International Application No. PCT/EP2018/069358, filed on Jul. 17, 2018. 11 pages.

\* cited by examiner

HEALTH MONITORING DEVICE INCLUDING PINNED PHOTODIODE

RELATED APPLICATIONS

This application is a Continuation of U.S. Non Provisional Application No. 16/631,642 filed on Jan. 16, 2020, which is a § 371 National Phase Application of International Application No. PCT/EP2018/069358, filed on Jul. 17, 2018, now International Publication No. WO 2019/016191 A1, published on Jan. 24, 2019, which claims priority to International Application No. PCT/EP2017/068502, filed on Jul. 21, 2017, all of which are incorporated herein by reference in their entirety.

DOMAIN OF THE INVENTION

The present invention relates to the domain of CMOS sensors for biomedical applications, especially health monitoring.

Nowadays, health monitoring is becoming increasingly important, given both the ageing of population and the combined action of an increase in obesity level and cardio-related pathologies, i.e. cardiovascular diseases. The healthcare industry is becoming more dependent on new methods to monitor patients.

This, along with an increased interest in fitness and wellness, is calling for more affordable and precise health monitoring devices, especially when wearable.

In such a context, photoplethysmography (PPG) is known and appears to be a key technology allowing non-invasive monitoring of vital biological indicators such as heart rate (HR), blood oxygen saturation ($S_pO_2$), respiration rate (RR), and arterial pressure (AP).

A standard PPG system comprises pulsed LEDs synchronized with a photo-sensor and a processing chain. The LEDs diffuse light in the human skin. Processing the signal held by the reflected diffused light allows the extraction of some vital parameters.

A standard PPG measures some cardiac parameters by simply shining light at specific wavelengths, on a tissue and reading out either the reflected light or the transmitted light through the tissue. A big part of the light is absorbed by the tissue whilst a small amount of it reaches the detector. Once at the detector the light is converted into a photo-generated current, eventually filtered and processed by an acquisition chain, i.e. an electronic circuit. To achieve this, a standard PPG comprises at least two light emitting diodes (LEDs), and one broadband "Photodiode" (PD).

Typically, two LEDs shine light in time division multiplexing, i.e. in out-of-phase, at two different wavelengths, e.g. visible and mid-infrared, taking advantage of the different absorption properties of the molecules circulating in the blood and particularly of the oxygenated haemoglobin ($HbO_2$), and the deoxygenated haemoglobin (Hb). The "counting" of the $HbO_2$ molecules over the overall haemoglobin ones $$\left( \frac{HbO_2}{Hb + HbO_2} \right)$$

gives the oxygen saturation level ($S_pO_2$), said parameter reporting the amount of oxygen flowing in the blood. The tissue being a quite complex environment with a lot of absorbing materials, the power of the emitted light should be large enough to allow enough photons impinging on the detector (the majority of them will get absorbed by the tissue). The biggest bottlenecks of PPG based system is then the LED power consumption.

This is why current medical PPG systems based on conventional PN or PIN diodes, such as those disclosed in US 2016/183813 are incompatible with portable or wearable solutions.

And although recently introduced research works present system-on-board (SOB) solutions relying on photodiodes, such SOB present relatively complex circuitry. Moreover, the commercially available smartwatches and other connected clothes fall short of meeting customer requirements in terms of reliability, precision and battery lifetime.

The present invention aims to address these drawbacks.

SUMMARY OF THE INVENTION

More precisely, the present invention relates to a photoplethysmography (PPG) sensing device configured to output a signal comprising a DC component and an AC component, said device comprising:
- a pulsed light source, adapted to be pulsed-on or pulsed-off,
- at least one pixel for light-to-charge conversion to create photo-generated electrons,
- each pixel being synchronized with said pulsed light source.

It is mainly characterized in that each pixel comprises:
- a pinned photodiode (PPD) comprising a well and having two electronic connection nodes,
- a sense node (SN), said sense node being a $n^+$-p junction capacitance whose role is to convert the photo-generated electrons in the pinned photodiode (PPD) well into a voltage, by the means of the conversion gain of said capacitance, and
- a Transfer Gate (TGtransfer) transistor, having its source electronically connected to one electronic connection node of said pinned photodiode (PPD), and being configured to act as a transfer gate (TG) between said pinned photodiode (PPD) and said sense node (SN), allowing the photo-generated electrons to sink when the light is pulsed-off, the photo-generated electrons integration when the light is pulsed-on and the transfer of at least part of the integrated photo-generated electrons to said sense node for a read-out, wherein the grid of the TGtransfer transistor is preferably electronically connected to a DC power source (V_TGtransfer), of which the value can be dynamically adapted.

As a result of using a pinned photodiode, which is a very different device to a conventional PN or PIN photodiode, it is possible to use much shorter illumination pulses, in the order of microseconds. This reduces power consumption significantly over prior art PN/PIN diode-based PPG devices, rendering them compatible with small and lightweight devices which can be carried on the person. Furthermore, and as explained further below, by exploiting a particular property unique to PPD's and not present in conventional PN/PIN diodes, the signal to noise ratio can be massively improved at the level of the output from the PPD, by eliminating the DC portion of the signal at the point of readout of the PPD itself, entirely without any need for power-hungry signal processing downstream. The combination of these aspects surprisingly results in massive reduction of power consumption compared to existing PPG systems, rendering them suitable to be carried and worn permanently.

In one embodiment, each pixel further comprises:
a Sink (TGsink) transistor, having its source electronically connected to the other electronic connection node of said pinned photodiode (PPD), and being configured to act as a transfer gate (TG) between said pinned photodiode (PPD) and either a constant DC power source or a capacitance, allowing the photo-generated electrons to sink towards said constant DC power source or said capacitance when the light is pulsed-off and the photo-generated electrons integration when the light is pulsed-on.

In one embodiment, each of said pixels comprises at least one further pinned photodiode (PPD), arranged in parallel with said pinned photodiode (PPD) and connected to said sense node (SN) by means of a respective Transfer Gate (TGtransfer) transistor, each of said Transfer Gate (TGtransfer) transistors being configured to be operated synchronously, for instance by means of having their gates electrically connected together. Advantageously, each of said further pinned photodiodes (PPD) is connected to said constant DC power source or said capacitance, as appropriate, by means of a respective Sink (TGsink) transistor, the gate of each of said Sink (TGsink) transistors being configured to be operated synchronously. Such so-called macropixel structures increases the sensitivity by increasing the amount of photogenerated charge available while retaining simple circuitry.

Preferable, said pixels, whether incorporating single PPD's or multiples in macropixels, are disposed in an array, increasing the sensitivity of the device.

In one embodiment, the photoplethysmography (PPG) sensing device further comprises a processor (DSP) configured to average spatially outputs of the macro-pixels.

In one embodiment, the photoplethysmography (PPG) sensing device further comprises:
A first block (CDS1) comprising:
a capacitance ($C_{SH1}$) to store a value (V_reset) of the output signal of the photoplethysmography (PPG) sensing device, when the pulsed light source is off and the sense node (SN) well is empty, and
a capacitance ($C_{SH2}$) to store a value (V_amb+V_reset) of the output signal of the photoplethysmography (PPG) sensing device, when the pulsed light source is off, and the photoplethysmography (PPG) sensing device is just subject to ambient light, and to store a value (V_LED+V_amb+V_reset) of the output signal of the photoplethysmography (PPG) sensing device when the pulsed light source is on. The PPG device may also comprise:
A second block (CDS2) comprising:
a capacitance ($C_{SH4}$) to store the value (V_amb) of the difference between said value (V_reset) of capacitance ($C_{SH1}$) and said value (V_amb+V_reset) of capacitance ($C_{SH2}$), and
a capacitance ($C_{SH3}$) to store a value (V_LED+V_amb) of the output signal of the photoplethysmography (PPG) sensing device when the pulsed light source is on,
wherein said second block (CDS2) is constructed such that the difference of value between said value (V_LED+V_amb) of capacitance ($C_{SH3}$) and said value (V_amb) of capacitance ($C_{SH4}$) is send to an ADC to assess the voltage (V_LED) related to the pulsed light source (LED) only.

In one further embodiment, the photoplethysmography (PPG) sensing device comprises one single CDS block comprising:

a capacitance ($C_{SH1}$) to store a first value (V_LED1+V_amb+V_reset) of the output signal of the photoplethysmography (PPG) sensing device, when the pulsed light source is on during a first pulse and the sense node (SN) well has been allowed to integrate for a predetermined time period, and
a capacitance ($C_{SH2}$) to store a second value (V_LED2+V_amb+V_reset) of the output signal of the photoplethysmography (PPG) sensing device when the pulsed light source is on during a second pulse, and the sense node (SN) well has been allowed to integrate for said predetermined time period (i.e. for a predetermined time period with the same duration as that previously mentioned), and
wherein said block (CDS) is constructed such that a function off the difference of value between said first value (V_LED1+V_amb+V_reset) stored by capacitance ($C_{SH1}$) and said second value (V_LED2+V_amb+V_reset) stored by capacitance ($C_{SH2}$) is sent to an ADC to assess a voltage related to (V_LED2−V_LED1), proportional to the derivative of signal related to the pulsed light source (LED) only. This provides further useful information relating to the PPC signal.

In a yet further embodiment, the photoplethysmography (PPG) sensing device may comprise a single CDS block comprising:
a capacitance ($C_{SH1}$) to store a value (V_reset+V_amb) of the output signal of the photoplethysmography (PPG) sensing device, when the pulsed light source is off and the sense node (SN) well has been allowed to integrate for a predetermined time period, and
a capacitance ($C_{SH2}$) to store a value (V_amb+V_reset+V_LED) of the output signal of the photoplethysmography (PPG) sensing device when the pulsed light source is on, and the sense node (SN) well has been allowed to integrate for said predetermined time period (i.e. for a predetermined time period with the same duration as that previously mentioned) and
wherein said block (CDS) is constructed such that a function of the difference of value between said value (V_LED+V_reset+V_amb) stored by capacitance ($C_{SH1}$) and said value (V_reset+V_amb) stored by capacitance ($C_{SH2}$) is sent to an ADC to assess a voltage (V_LED) related to the signal related to the pulsed light source (LED) only.

All of these variants including one or more CDS blocks serve to filter out undesired DC components of the PPD signal, improving signal to noise ratio, with very few active components other than transistors acting as switches. This results in an excellent signal to noise ratio at an extremely low power consumption.

In one embodiment, the photoplethysmography (PPG) sensing device is built in CMOS technology, which is embedded in a system on chip (SOC).

According to another of its objects, the present invention relates to a method of operating a photoplethysmography (PPG) sensing device according to the present invention, comprising a step of:
in a transfer phase, setting the Transfer Gate (TGtransfer) transistor voltage to a value (V_TGtransfer) comprised between the well potential (V_well) of the pinned photodiode (PPD) and the voltage (V_TGsink) applied to the Sink transistor (TGsink) to allow only photo-generated electrons exceeding said offset to be transferred to the sense node (SN) for read-out.

This results in being able to eliminate a large proportion, if not all, of the unwanted DC component of the PPD's output at the level of the PPD itself, which massively improves the signal to noise ratio downstream, without requiring any power-hungry processing circuitry. Such operation is impossible with a conventional PN or PIN photodiode, which does not have a charge well, and in essence permit a rejection of the DC component of the signal, which is undesired and contains no exploitable information.

In one embodiment, the Transfer Gate (TGtransfer) transistor voltage is dynamically adapted.

In one embodiment, the method comprises a calibration step comprising the steps of:
A. setting the value (V_TGtransfer) of the DC power source to a predetermined value,
B. checking if the corresponding pixel response exceeds a predetermined threshold value, and
C. if the pixel response exceeds the said threshold value, repeating steps A and B until the corresponding pixel response is no longer exceeding the threshold.

This allows optimisation of the value of V_TGtransfer to maximise the signal to noise ratio without complex circuitry or power-hungry processing.

In one embodiment, the method comprises the steps of:
pulsing-off the pulsed light source, and
integrating charge in said pinned photodiode during a predetermined period of time (i.e. during a length of time with a predetermined duration);
transferring said charge to said sense node (SN) by means of said transfer gate transistor (TGtransfer) and storing said charge in a first capacitor (CSH1) so as to generate a voltage (V_amb) corresponding to ambient light; then (i.e. at a later timepoint, typically several tens of microseconds later)
pulsing-on the pulsed light source during said predetermined period of time (i.e. for a predetermined time period with the same duration as that previously mentioned),
Integrating charge in said pinned photodiode during said predetermined period of time (i.e. for a predetermined time period with the same duration as that previously mentioned);
transferring said charge to said sense node (SN) by means of said transfer gate transistor (TGtransfer) and storing said charge in a second capacitor (CSH2) so as to generate a voltage (V_amb+V_LED) corresponding to ambient light mixed with the pulsed light source; then
subtracting the voltage (V_amb) corresponding to the ambient light from the voltage (V_amb+V_LED) corresponding to the pulsing-on of the pulsed light source mixed with the ambient light to result in a voltage (V_LED) corresponding to a function of the detected light originating from the pulsed light source exclusively. This function is typically half the difference between (V_amb+V_LED) and (V_amb).

Alternatively the method may, comprise the steps of:
pulsing-on the pulsed light source,
Integrating charge in said pinned photodiode during a predetermined period of time;
transferring said charge to said sense node (SN) by means of said transfer gate transistor (TGtransfer) and storing said charge in a first capacitor (CSH1) so as to generate a voltage (V_amb+V_LED) corresponding to the ambient light mixed with the pulsed light source; then (i.e. at a later timepoint, typically several tens of microseconds later)
pulsing-off the pulsed light source, and
integrating charge in said pinned photodiode during said predetermined period of time (i.e. for a predetermined time period with the same duration as that previously mentioned);
transferring said charge to said sense node (SN) by means of said transfer gate transistor (TGtransfer) and storing said charge in a second capacitor (CSH2) so as to generate a voltage (V_amb) corresponding to ambient light; then
subtracting the voltage (V_amb) corresponding to the ambient light from the voltage (V_amb+V_LED) corresponding to the pulsing-on of the pulsed light source mixed with the ambient light to result in a voltage (V_LED) corresponding to a function of the detected light originating from the pulsed light source exclusively. This function is typically half the difference between (V_amb+V_LED) and (V_amb).

Alternatively, the method may comprise the steps of:
pulsing-on the pulsed light source,
Integrating charge in said pinned photodiode during a predetermined period of time;
transferring said charge to said sense node (SN) by means of said transfer gate transistor (TGtransfer) and storing said charge in a first capacitor (CSH1) so as to generate a voltage (V_amb+V_LED1) corresponding to the ambient light mixed with the pulsed light source; then (i.e. at a later timepoint, typically several tens of microseconds later),
pulsing-on again the pulsed light source, and
integrating charge in said pinned photodiode during said predetermined period of time (i.e. for a predetermined time period with the same duration as that previously mentioned);
transferring said charge to said sense node (SN) by means of said transfer gate transistor (TGtransfer) and storing said charge in a second capacitor (CSH2) so as to generate a voltage (V_amb+V_LED2) corresponding to ambient light mixed with the second sample of pulsed light source; then
subtracting the voltage (V_amb+V_LED1) from the voltage (V_amb+V_LED2) to obtain a function of the difference between (V_LED1) and (V_LED2) which is a function of the derivative of the signal related to the light received from the pulsed light source (LED) only, typically half the difference between the two voltages related to the part of the signal due to the LED illumination. This provides useful, exploitable information.

Alternatively, the method may comprise the steps of:
pulsing-off the pulsed light source,
Integrating charge in said pinned photodiode during a predetermined period of time;
transferring said charge to said sense node (SN) by means of said transfer gate transistor (TGtransfer) and storing said charge in a first capacitor (CSH1) so as to generate a voltage (V_reset+V_amb) corresponding to the ambient light mixed with the reset voltage (V_reset); then (i.e. at a later timepoint, typically several tens of microseconds later)
pulsing-on the pulsed light source, and
integrating charge in said pinned photodiode during said predetermined period of time (i.e. for a predetermined time period with the same duration as that previously mentioned);
transferring said charge to said sense node (SN) by means of said transfer gate transistor (TGtransfer) and storing said charge in a second capacitor (CSH2) so as to generate a voltage (V_amb+V_reset+V_LED) corresponding to ambient light mixed with the reset voltage and the signal related to the pulsed light source (LED); then subtracting the voltage (V_reset+V_amb) from the voltage (V_amb+V_reset+V_LED) to obtain a function of the signal related to the pulsed light source (LED) only.

These variants significantly improve the signal-to-noise ratio by eliminating the DC component to a minimum, and the variant relating to the derivative provides further exploitable information relating to the desired signal.

Advantageously, said subtraction is carried out by connecting said first capacitor (CSH1) and second capacitor (CHS2) in parallel such that the polarity of one capacitor is inverted with respect to the other, a point of connection common to both capacitors (CSH1; CSH2) giving a voltage value corresponding to half of the difference between the voltage previously across each capacitor (CSH1; CSH2). This is extremely simple and passive, maintaining power consumption at a bare minimum.

Preferably, the photoplethysmography (PPG) sensing device comprises a plurality of pixels, which may be macro-pixels, said method further comprising a step of averaging spatially the outputs of each pixel, for instance macro-pixel in analog domain by means of passive switch-capacitor network.

Advantageously, the present invention is non-invasive.

Further characteristics and advantages of the present invention will be described in the detailed description, with reference to the drawings.

DRAWINGS

Figure 2A:
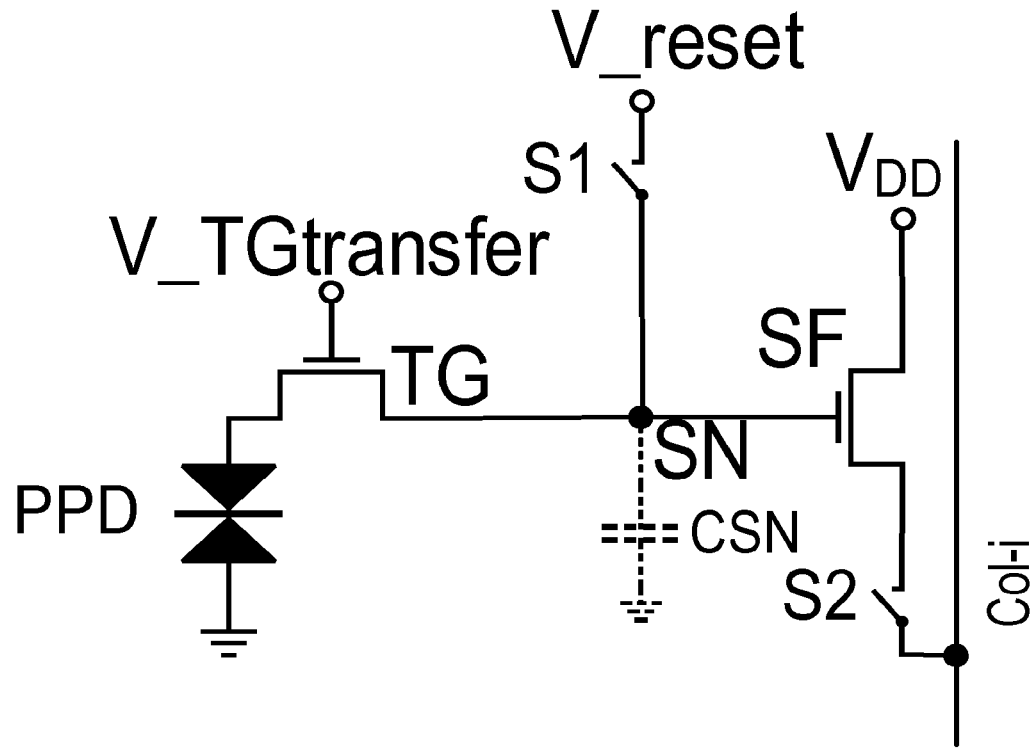
Figure 2B:
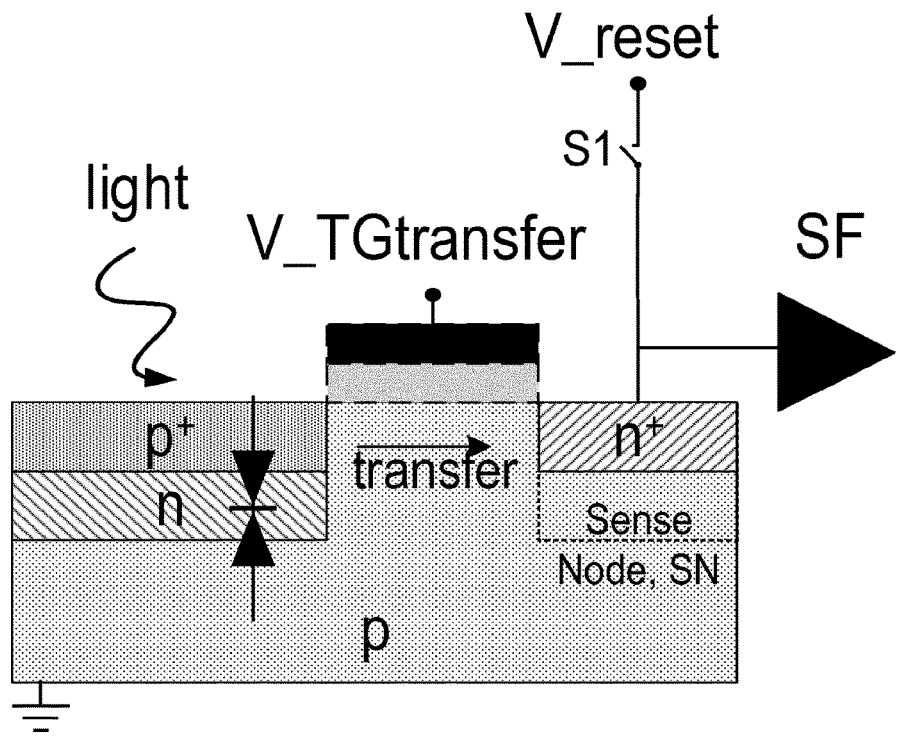
Figure 3:
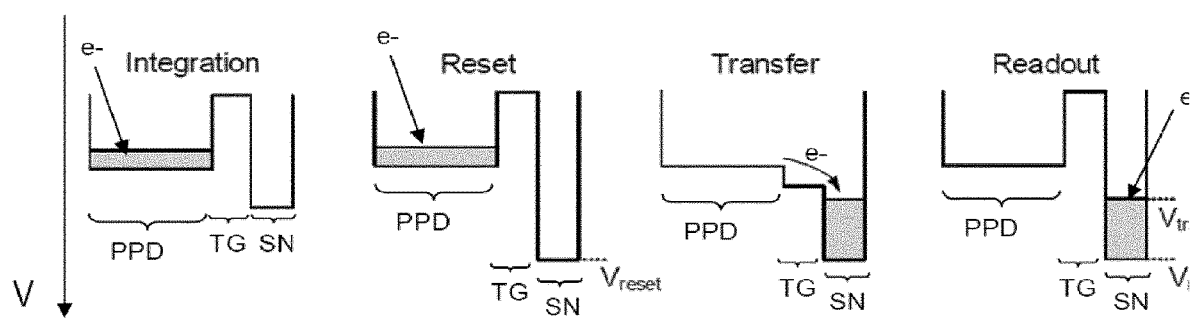
Figure 4A:
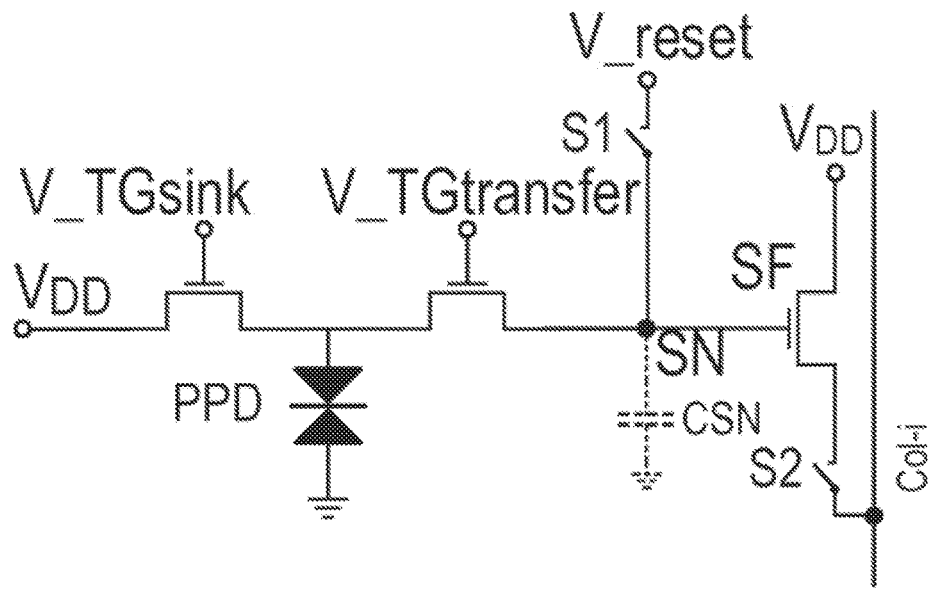
Figure 4B:
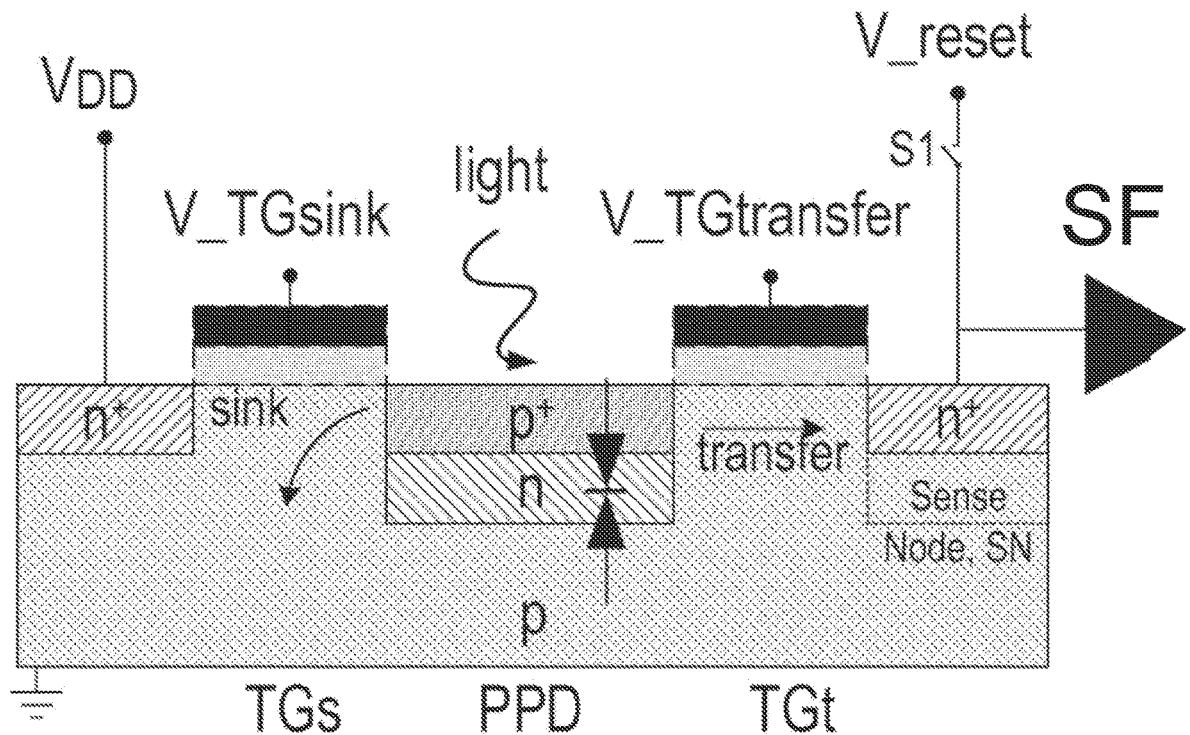
Figure 5A:
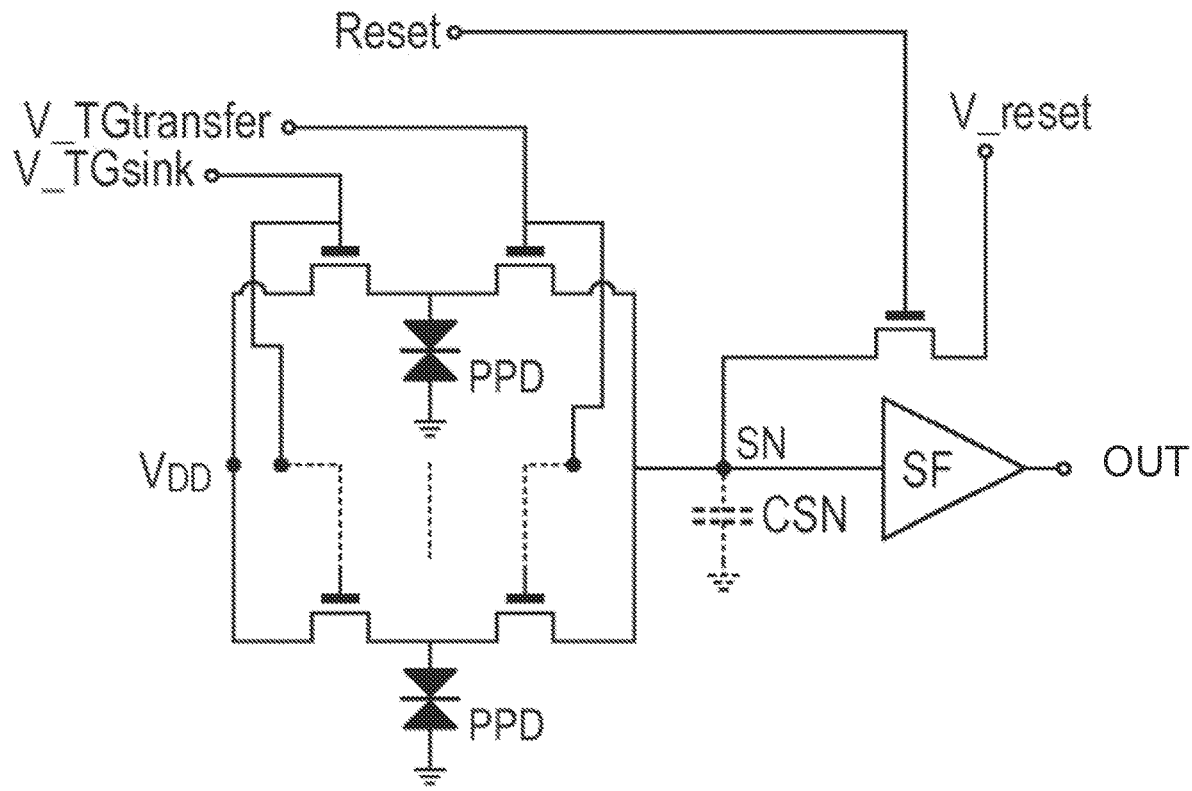
Figure 5B:
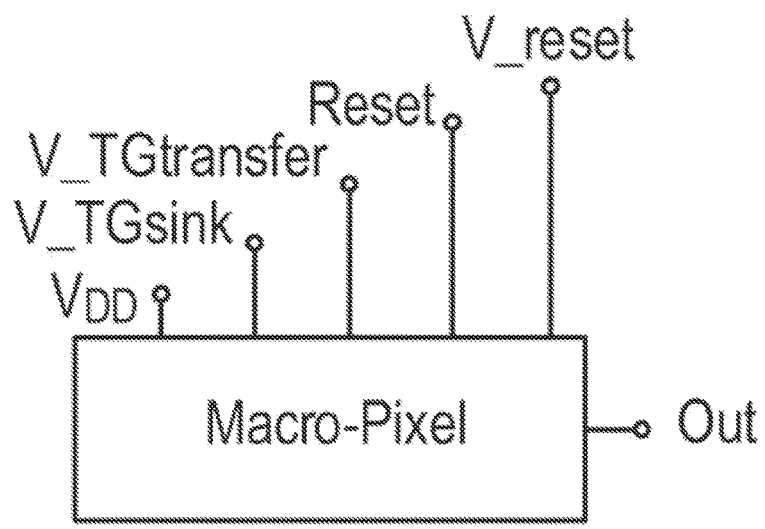
Figure 6:
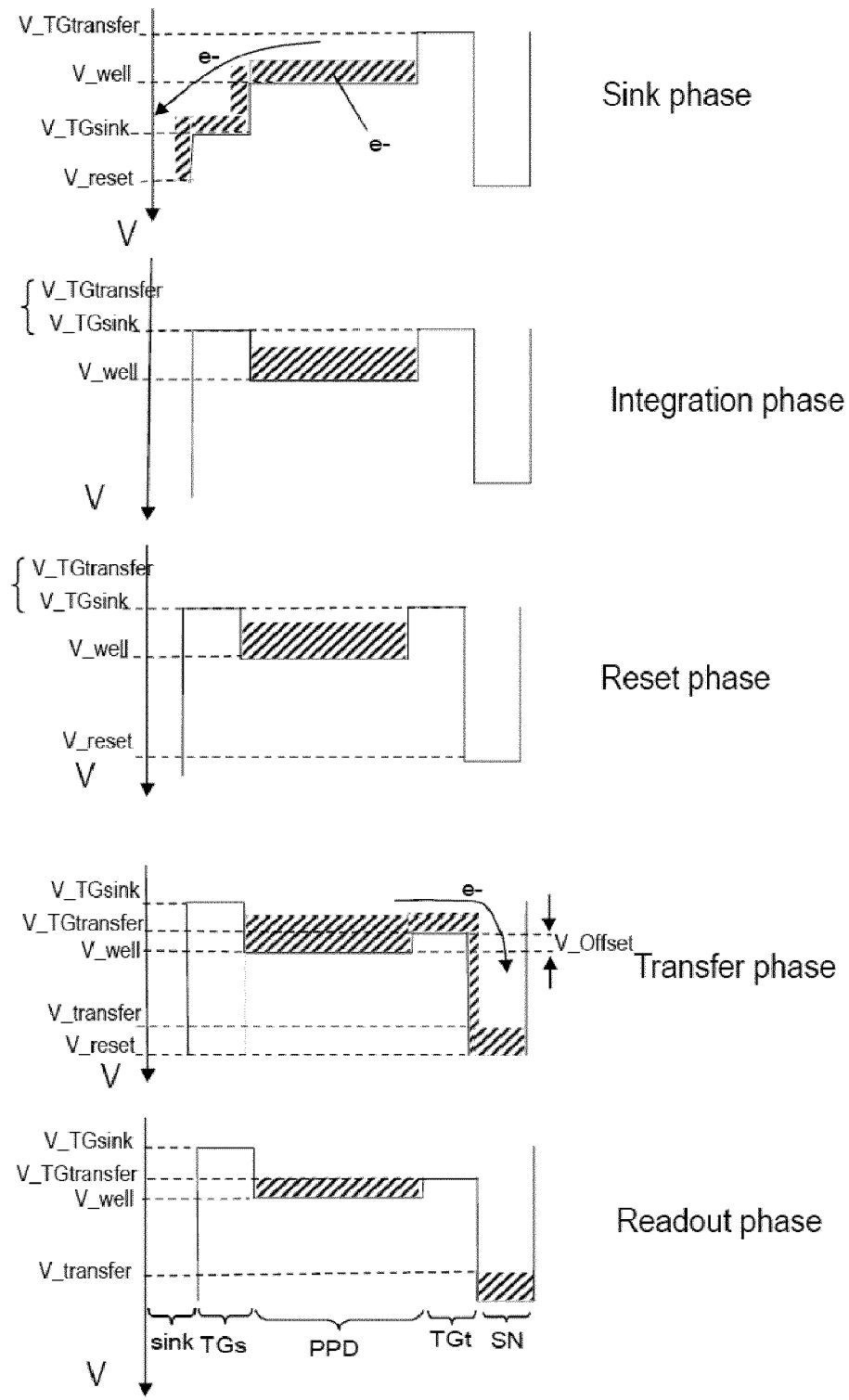
Figure 7A:
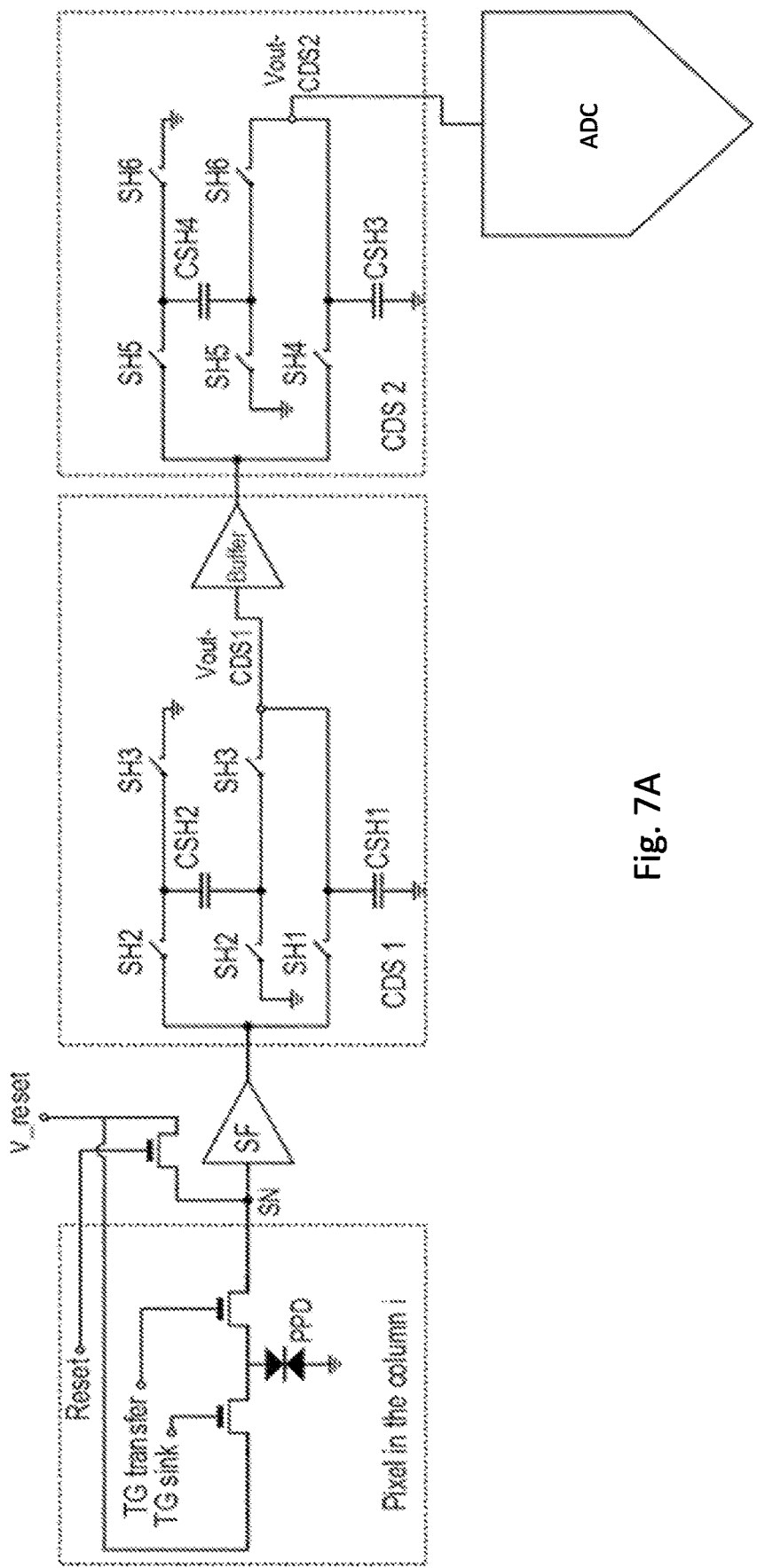
Figure 7B:
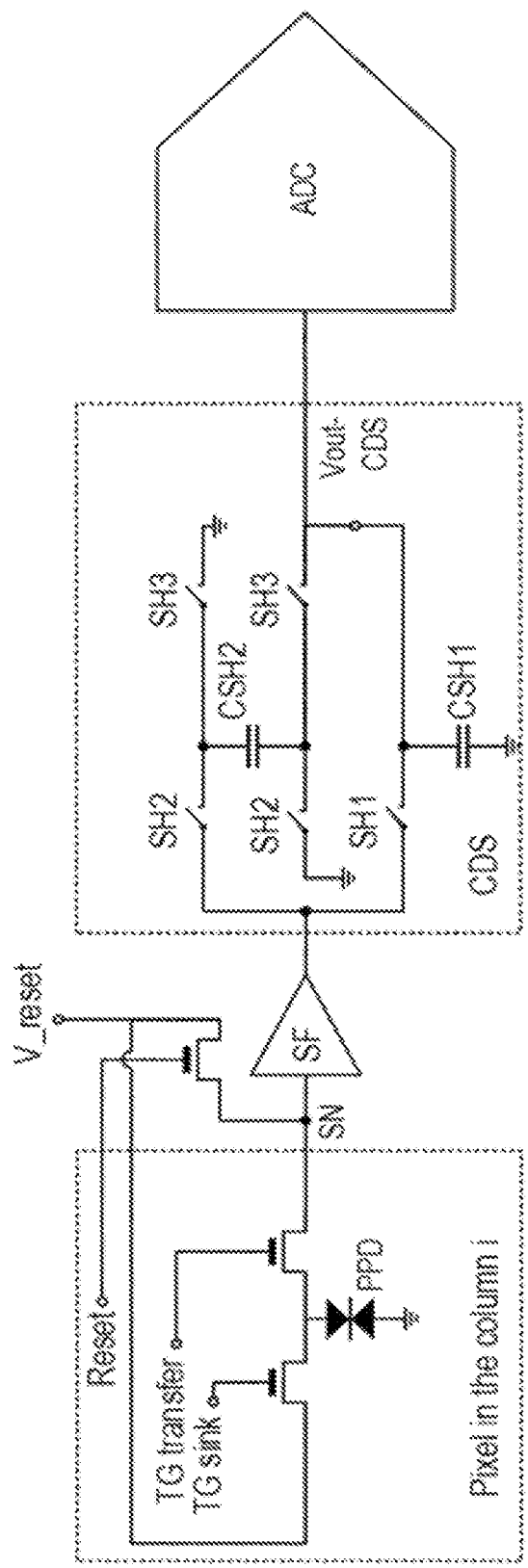
Figure 8A:
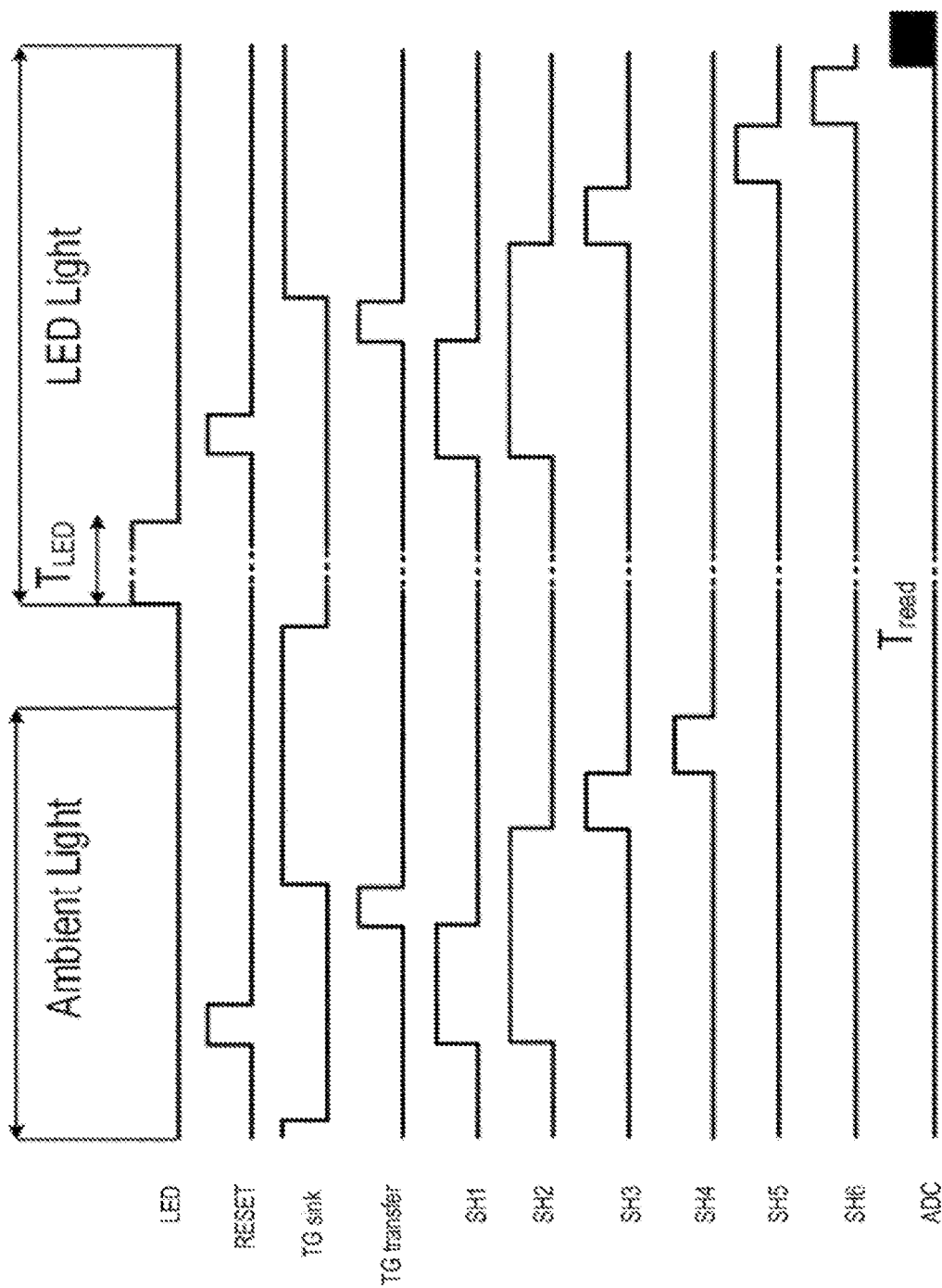
Figure 8B:
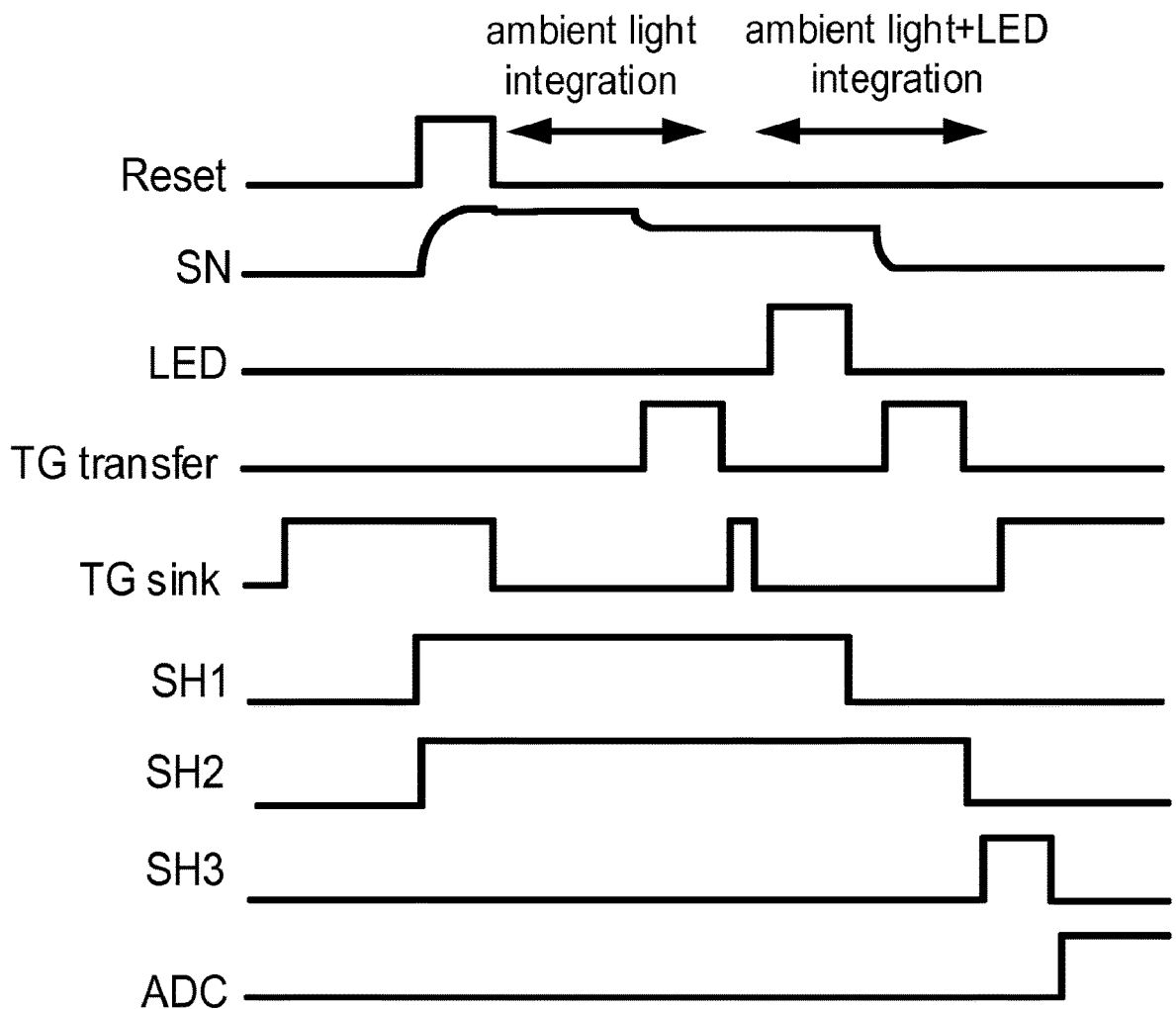
Figure 8C:
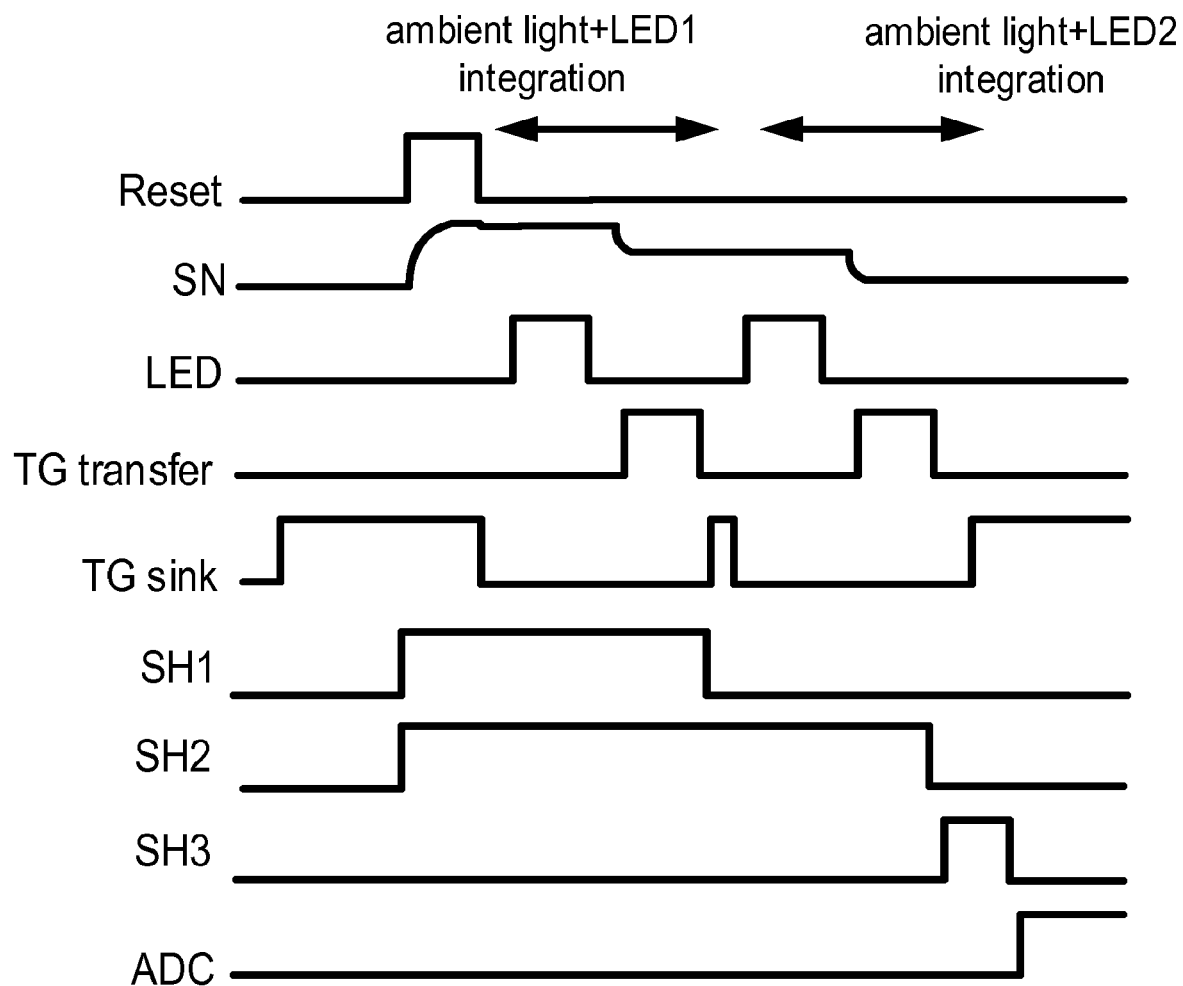
Figure 8D:
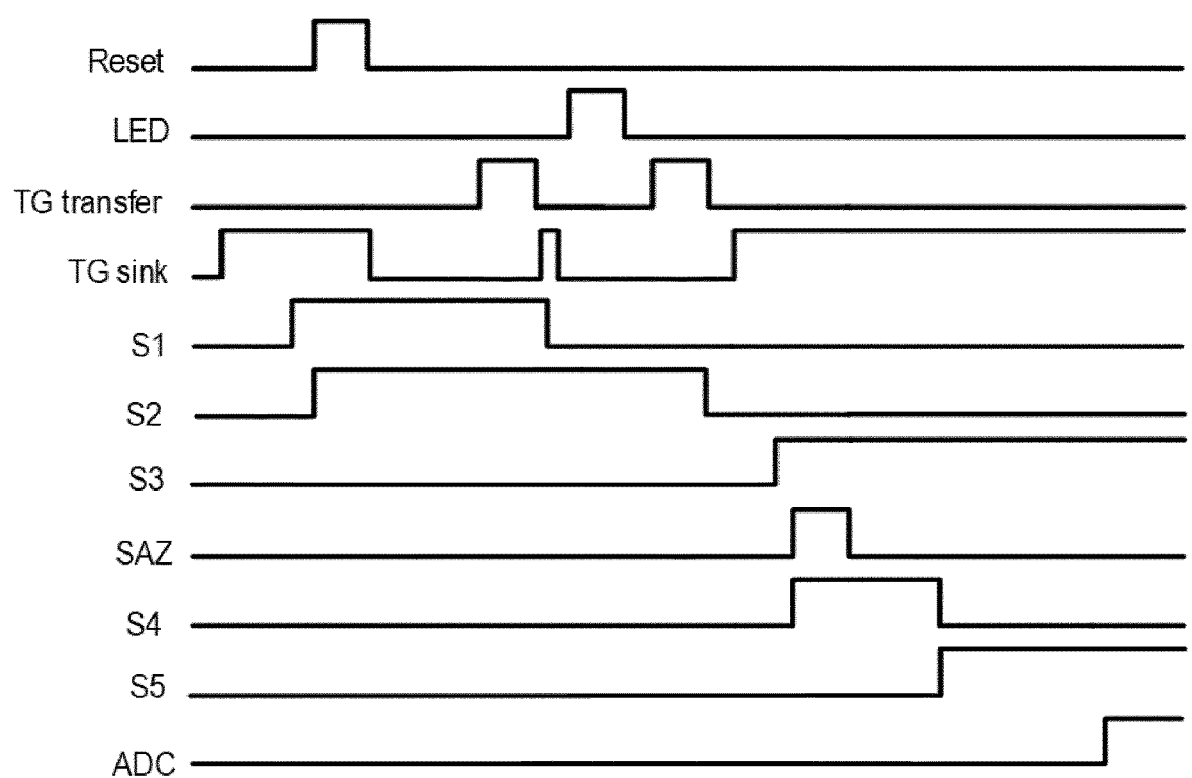
Figure 9A:
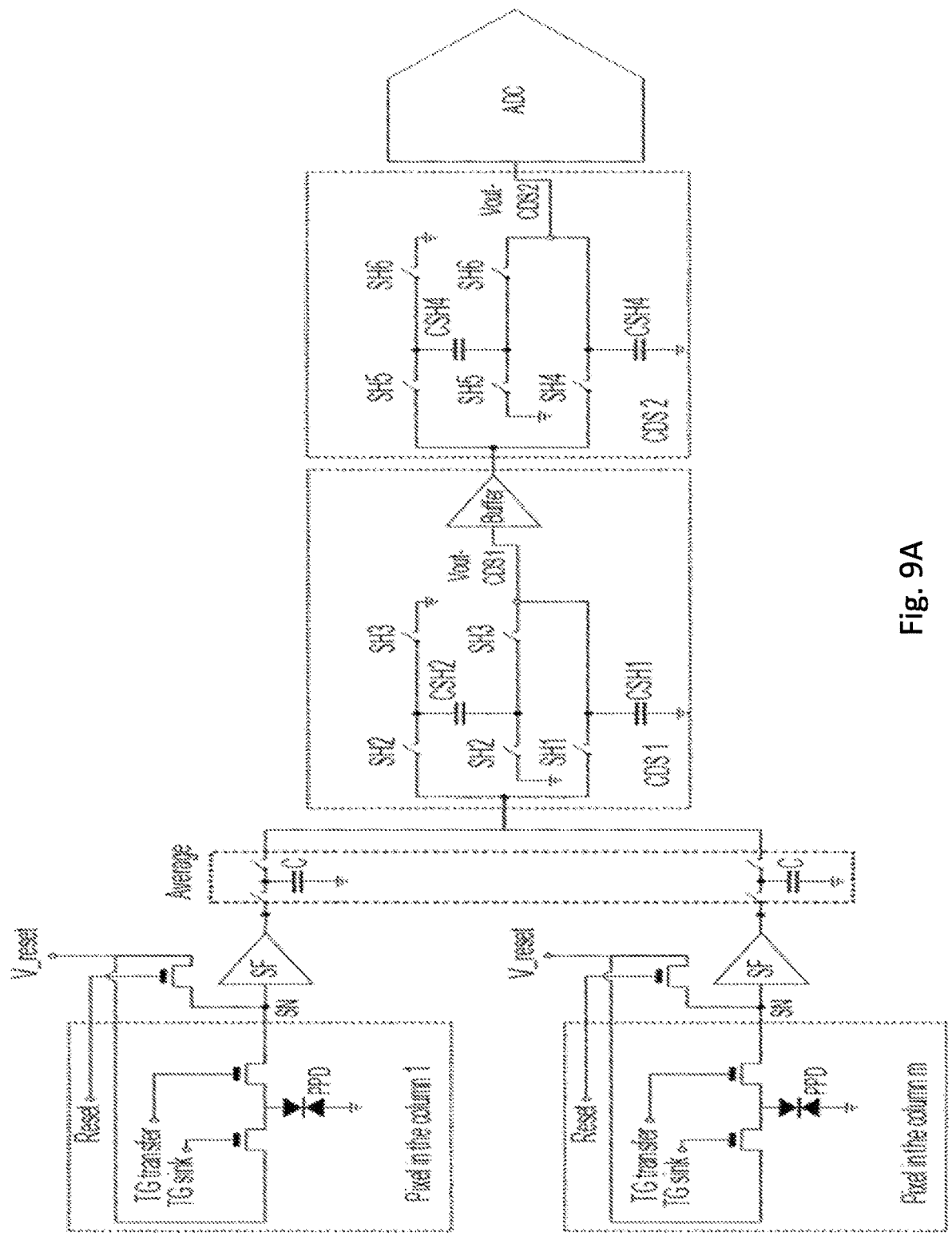
Figure 9B:
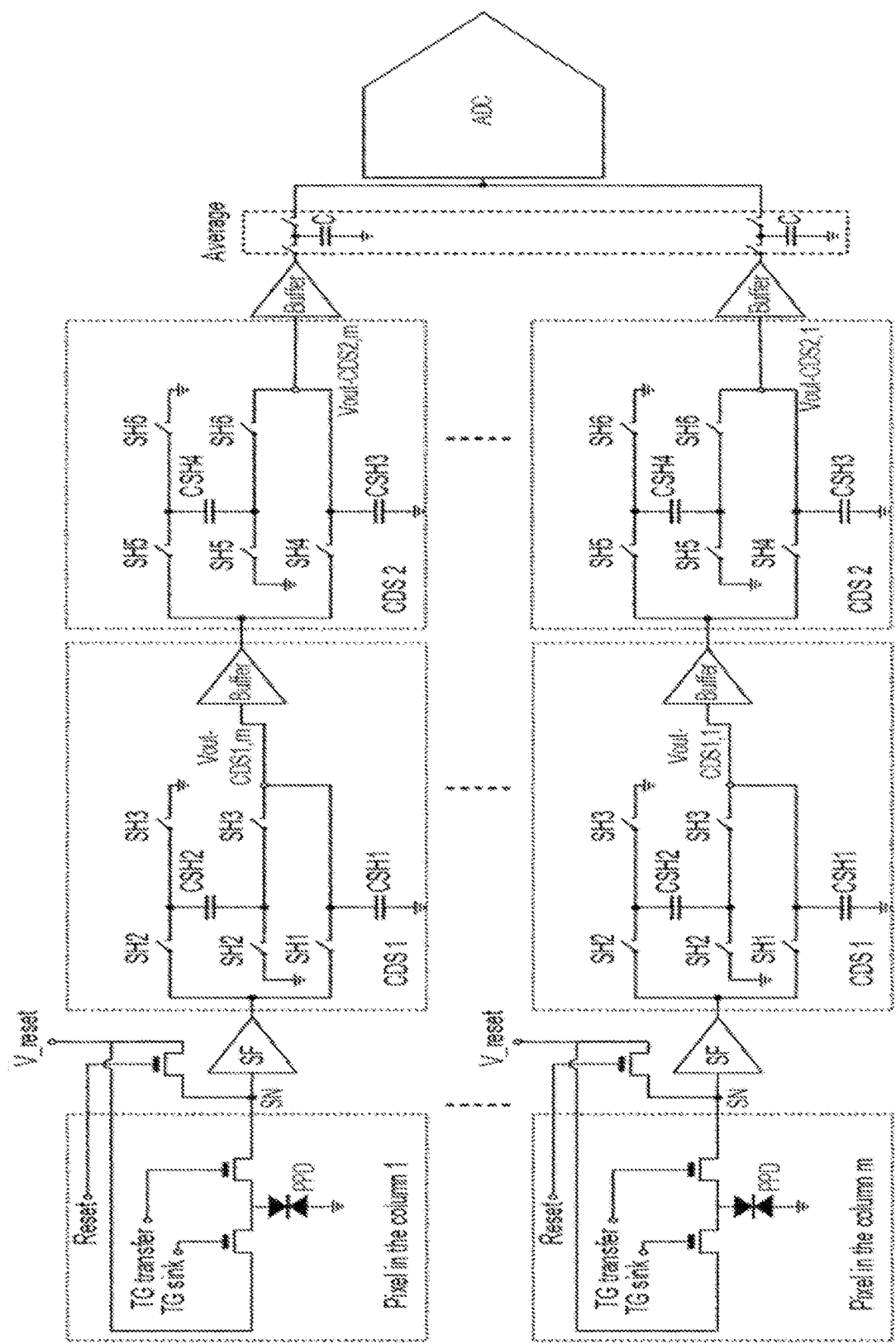
Figure 9C:
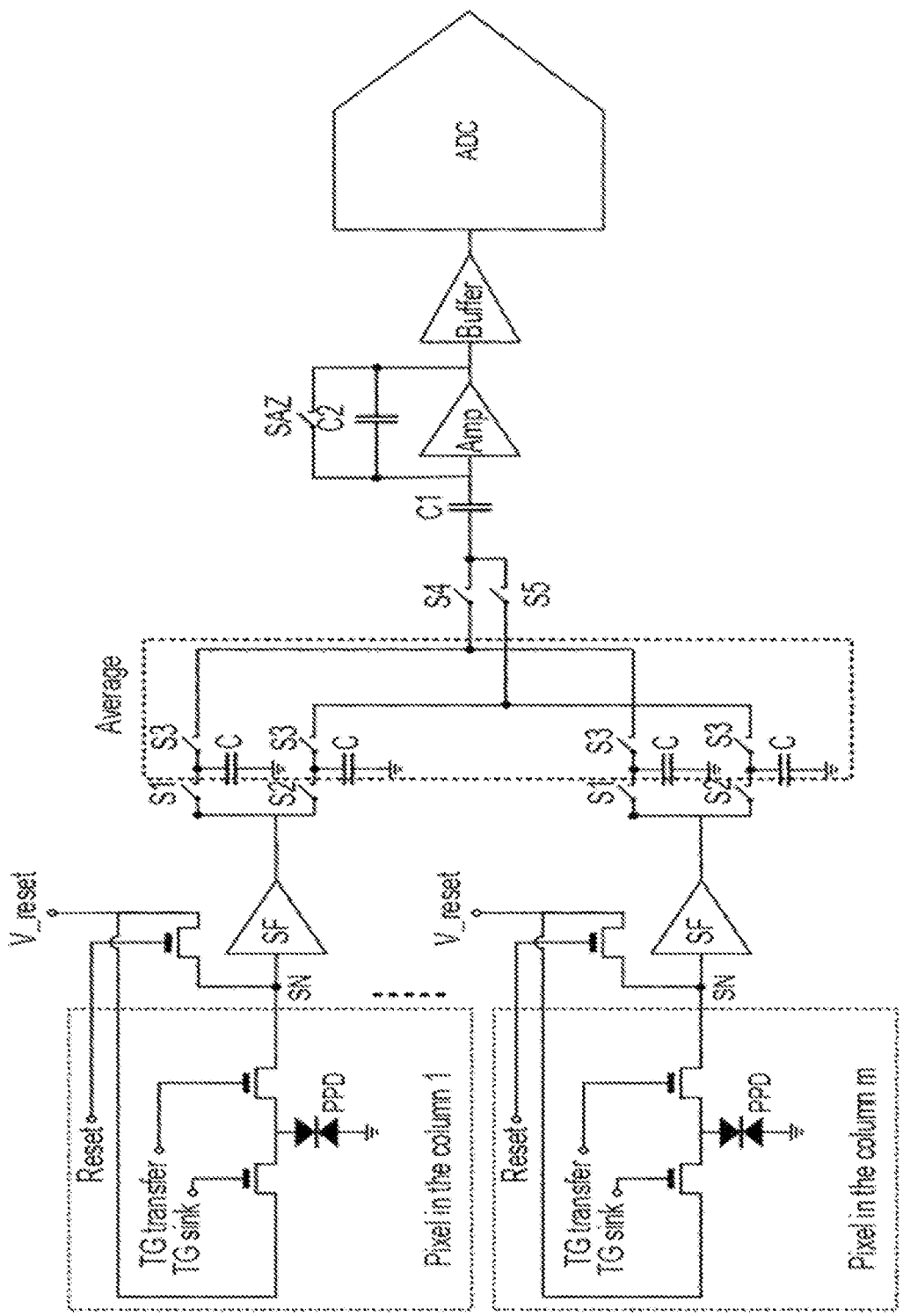
Figure 10:
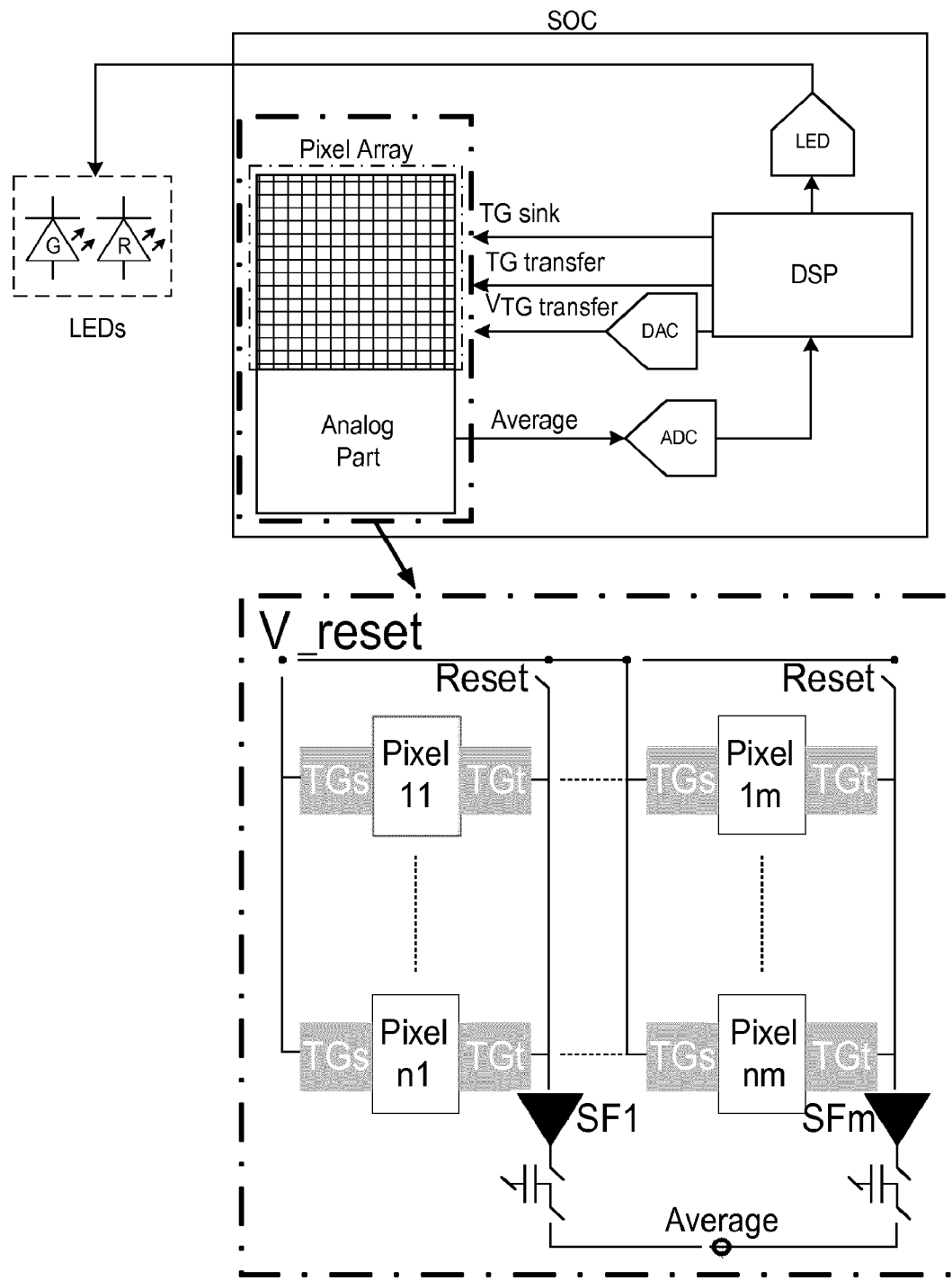
Figure 11:
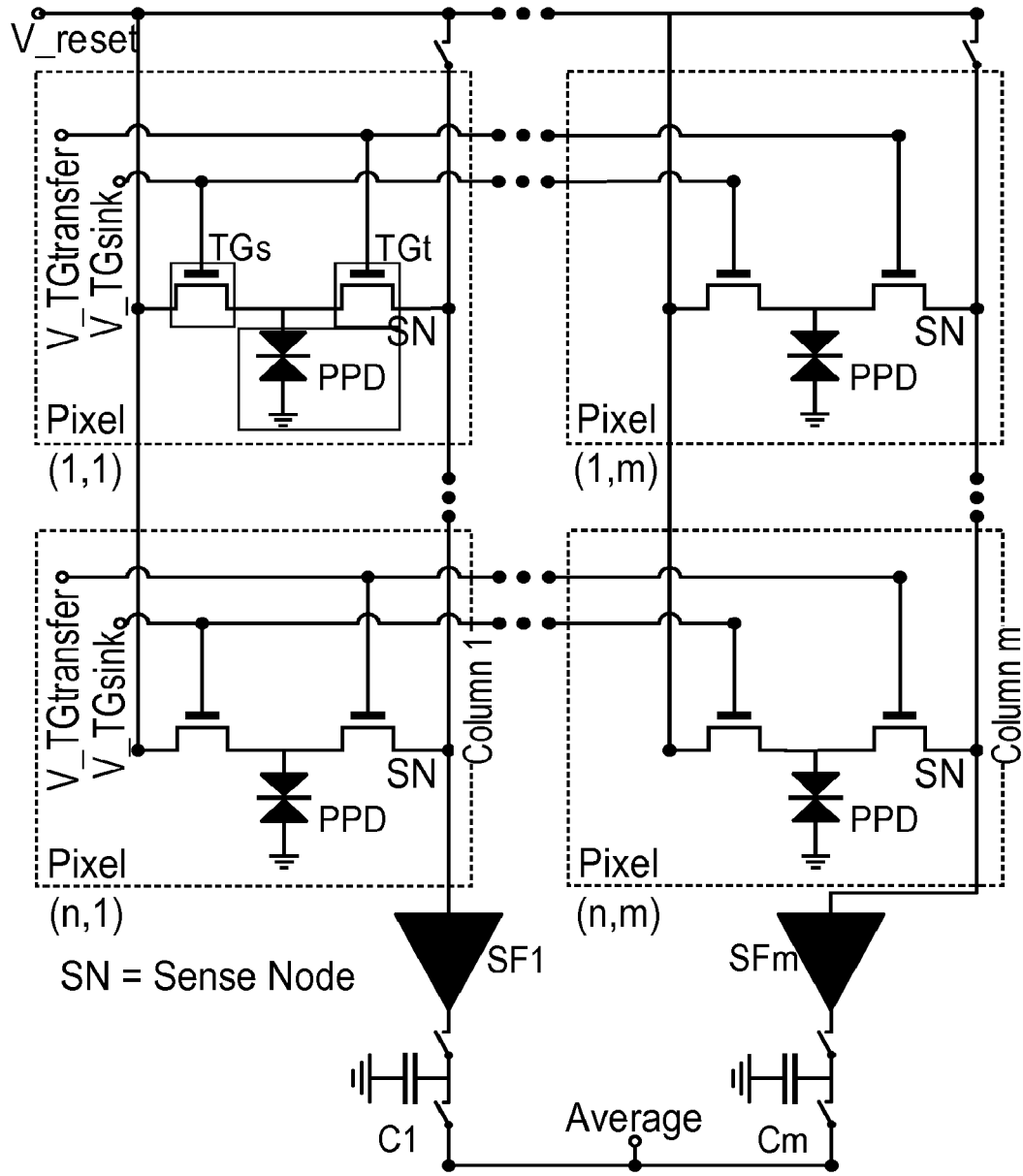

FIG. 1 illustrates a graph of conventional PPG photo-generated current,

FIG. 2A illustrates an electronic circuit corresponding to a pixel according to one embodiment of the present invention, FIG. 2B illustrates part of the pixel according to FIG. 3A in a cross-section view, FIG. 3 illustrates the different potentials and corresponding transfer of electrons within a pixel illustrated in FIG. 3 in successive phases of operation from left to right, FIG. 4A illustrates the electronic circuit of a pixel structure according to a further embodiment of the invention, FIG. 4B illustrates part of the pixel according to FIG. 4A in a cross-section view FIG. 5A illustrates the electronic circuit of a macro-pixel structure FIG. 5B illustrates a block diagram of the macro-pixel structure of FIG. 5A FIG. 6 illustrates the different potentials and corresponding transfer of electrons within a pixel or macro-pixel in successive phases of operation from top to bottom, FIG. 7A illustrates one embodiment of an electronic circuit designed to subtract an offset from the output of a pixel of an array, FIG. 7B illustrates a second variant of an electronic circuit designed to subtract an offset from the output of a pixel of an array, FIG. 8A illustrates one timing diagram to operate the electronic circuit of FIG. 7A, FIG. 8B illustrates one timing diagram to operate the electronic circuit of FIG. 7B, FIG. 8C illustrates one timing diagram to operate the electronic circuit of FIG. 7B to obtain the derivative of the PPG signal FIG. 8D illustrates one timing diagram to operate the electronic circuit of FIG. 9C, FIG. 9A illustrates one embodiment of an electronic circuit designed to average the outputs of pixels before multiple sampling, FIG. 9B illustrates an embodiment of an electronic circuit designed to average the outputs of pixels after multiple sampling, and FIG. 9C illustrates an embodiment of an electronic circuit designed to average the outputs of pixels before multiple sampling and optimized to operate with the timing diagrams of FIGS. 8,8C and 8D, FIG. 10 illustrates an SOC according to one embodiment of the present invention, and FIG. 11 illustrates an electronic circuit corresponding to an array of pixels distributed in an array (m, n) of m column and n rows.

DETAILED DESCRIPTION

In the foregoing description and in the figures, whenever a switch is mentioned or illustrated, it typically is implemented as a transistor such as a FET, MOSFET or similar.

PPD Photo-Generated Current

FIG. 1 illustrates a classic PPG photo-generated current (not to scale), which corresponds to photons coming out of the tissue and converted into electrons thanks to the PD quantum efficiency. "PPG photo-generated current" is also called "current" or "PPG photo-generated signal", "PPG signal" or "signal" in the present description.

This photo-generated current comprises mostly a large direct current (DC) component, due to the combined action of the tissue (DC tissue), the venous blood layer (DC ven.) and the non-pulsatile arterial blood layer absorption (DC art.). Just a small amount of this photo-generated current (FIG. 1, on top) is a small alternating current (AC) which contains the signal of interest.

Typically, depending on the LED wavelength, the total DC component (DC tissue+DC ven.+DC art. with reference to FIG. 1) can be from 20 to 500 times larger than the AC component.

Such a discrepancy in values gives rise to:
  either tough design and filtering stratagems with the aim of amplifying the tiny AC component and reducing in parallel the DC component; or
  processing in the digital domain, at the price of Analog-to-Digital Converters (ADCs), needing large bit resolution, large power consumption and more silicon area, or weak signal-to-noise (SNR) and bad performances.

Indeed for PPG applications, the AC is the component of the photo-generated current which is needed to enable health monitoring. For instance, the AC component comes out of the pulsation of the blood in the arteries and is used to determine the heart rate by measuring the distance between two consecutive AC peaks. It is also used to determine the oxygen saturation level, said level being proportional to the logarithmic ratio between the absolute maximum and the absolute minimum value of the full photo-generated signal.

One of the challenges of a PPG signal relates to its dynamic range (DR), which is the ratio between the largest and the smallest values that said signal can assume.

Different solutions, each with a corresponding electronic circuit, exist but none of them is satisfactory enough.

For instance:
  a first solution, based on a logarithmic transimpedance photoreceptor, has bandwidth that changes linearly with the light intensity, which is an undesirable property. For instance, a same image sensor would give different results depending on the skin pigmentation of the user;

an improved solution of the first solution leads to interesting results but at a price of an overall power consumption which is quite high (about 4.5 mW) and an analog circuit which is quite complex;

another solution, based on a forward-path and a feedback-path reached a sub-mW power consumption, where instead of measuring the DC component and the AC component of the photocurrent, the feedback-path sets the DC photocurrent to a desired value, called reference current, which is the same for both the visible and IR channels. Such a solution allows for the removal of the DC in a quite easy way but at a price of a complex electronic circuit and a control loop where any layout mismatch or simply charge injection errors may result into a large offset errors;

another solution demonstrates that converting to digital the DC component of the PPG signal can resolve into the saturation of the ADC resolution. This suggests, in order to exploit the ADC full dynamic range, eliminating the DC before the ADC conversion and adding it back to the AC component afterwards, in the digital domain. But such a solution may lead to weak SNR and bad performances;

another solution based on an Error Amplifier also uses a feedback loop which controls the photoreceptor, but the efficiency of such technique gets weaker as the DC current gets smaller;

another solution is based on a Dynamic-Range Enhancer technique but also faces issues such as more complexity (additional blocks), lower speed and larger power.

To address this, the present invention proposes a new photonic sensing technology to read-out a PPG signal, especially by means of a system-on-chip (SOC) which can be fabricated in a standard CMOS technology, and having low-noise and low-power signal processing chain, a higher sensitivity and a reliable measurement at lower light levels from the LEDs.

The proposed solution, based on a PPG sensor comprising at least a pinned photodiode (PPD) instead of conventional single PD, enables to remove most of the DC component of a PPG signal as explained here after. The use of a PPD rather than a convention PN or PIN photodiode enables elimination of the DC component of the signal without complex and power-hungry circuitry, signal processing or similar, by exploiting the unique properties of PPD's which are not exhibited by PN or PIN photodiodes.

PPD Based Image Sensor

A first embodiment relates to a single transfer gate pixel arrangement.

A PPD comprises a p+-n-p junction (n-p junction buried under a shallow highly doped p+), as shown in FIG. 2B which illustrates a first embodiment of a pixel. The substrate in which the PPD is formed is of p-type doped semiconductor material, and is grounded, leaving the p+ doped zone essentially floating. This forms a charge well in which photogenerated charge accumulates, increasing the voltage at the p+ layer as the charge accumulates. In essence, the p+-n-p doped structure formed in the thickness of the substrate essentially forms two diodes arranged cathode-to-cathode, the n layer being shared between both, as illustrated schematically by means of the two nose-to-nose diode symbols on FIG. 2B (note: this symbol is schematic and does not indicate extra components, and merely illustrates the function of the layers and their junctions). This nose-to-nose diode symbol is unconventional, and has been used in the circuit diagrams of various figures to represent the PPD and to distinguish it from conventional PN and PIN photodiodes of the prior art, which generate a flowing charge in response to impinging light. In other words, in the case of a PPD, if the charge cannot flow out of said PPD, it is integrated as it accumulates in the PPD "charge well".

According to this first embodiment, a PPD is electronically connected to the source of a transistor, called Transfer Gate transistor, or TGtransfer transistor, which acts as a transfer gate (TG) between said PPD and a Sense Node, described later. As can be seen from FIG. 2B, the TGtransfer transistor is a field effect transistor (FET) arranged immediately laterally-adjacent to the P+zone of the PPD on the same substrate, which serves to be able to selectively "empty" the charge well.

The grid of the TGtransfer transistor is electronically connected to a DC power source called V_TGtransfer, of which the value can be dynamically adapted.

The TGtransfer transistor is used to control the potential barrier at one edge of the PPD, the other edge being electronically connected to the ground (FIG. 2A).

Adjusting the TG potential thanks to the TGtransfer transistor enables adjusting a DC Offset (FIG. 1), which is a predetermined DC voltage that is removed from the signal (DCtissue+DC ven.+DC art.+AC), and which can be set by calibration. It is then possible to remove from the PPG signal a predetermined part equal to said DC offset, as early as possible, and without any signal processing. In essence, this is an entirely passive method of massively improving the signal to noise ratio (the AC component being signal and the bulk of the DC component being noise) by simply setting the transfer gate potential when the PPD "charge well" is emptied. To the Applicant's knowledge, such an exploitation of the properties of a PPD is heretofore unknown, and has specific advantages in the context of a PPG.

With reference to FIG. 1, as a result, the PPG signal sent out for sensing is just the top part of the signal above the offset threshold; the DC offset is "removed" from the signal at the pixel level, and not sent out of the PPD for sensing. As a result, no signal processing to remove the DC component downstream of the sense node is required.

When this potential barrier surrounding the PPD, is lower than the well potential $V_{well}$ of the PPD, the photogenerated electrons are kept within that well. Typically, the potential barrier surrounding the PPD is kept at a slightly negative value by means of the TGtransfer transistor, at least in the integration phase described here under.

The other side of the TGtransfer transistor, in this case the drain, is electronically connected to a Sense Node (SN), see FIGS. 2A and 2B. The sense node (SN) is a $n^+$-p junction (see FIG. 2B) which by definition forms a capacitance CSN whose role is to convert the photo-generated (integrated) electrons in the PPD well into a voltage, by the means of the conversion gain of said capacitance CSN.

As illustrated in FIG. 2A, a pixel also comprises a source follower SF, which is a transistor electronically connected on the one side to a DC power source VDD and on the other side to a reading line Col-I through a switch S2, which may for instance be a transistor such as a FET. Switching on S2 enables reading the pixel illustrated on FIG. 3A, and is optional.

Switch S1 on FIG. 2A enables, when closed, imposing a V_reset voltage value to the Sense Node, V_reset being a constant DC power source. To this effect, switch S1 may be a transistor such as a FET.

Operating the pixel of FIG. 2A is illustrated on FIG. 3, which illustrates the different potentials and corresponding transfer of electrons within such a pixel in four phases of operation.

In an integration phase:
the PPD is illuminated with ambient light (if present) and LEDs light,
V_TGtransfer is set to low voltage to close the TGtransfer transistor and to create a barrier of potential,
S1 is open.

The potential barrier surrounding the PPD is kept lower than the well potential $V_{well}$ of the PPD. Accordingly the PPD generates photo-generated electrons, which are kept and accumulated within the PPD well.

Preferably the LEDs emit synchronously (in phase). This way, the LEDs consume power only when really needed. The integration phase typically lasts a hundreds of ns to several microseconds, i.e. from about 200 ns to 3 µs, preferably from 300 ns to 2 µs. Such a low integration time is possible thanks to the complete decoupling between the electronic readout chain and the PPD. In a standard PPG sensor based on a conventional PN or PIN photodiode, such a small integration time would require a much faster readout circuitry and hence much more power consumption. Note that a typical pulse time in state of the art commercially available products is 400 µs.

Successively to the integration phase, in a reset phase:
Preferably LEDS are off, which saves power, but is not essential
V_TGtransfer is kept to a low voltage,
S1 switch is closed.

This way, the voltage of the sense node SN is increased and set to V_reset value, draining all electrons (if any) within the SN well to the V_reset DC power source, but photo-generated electrons are still kept within the PPD well during the reset phase.

Then the reset switch S1 is opened for a predetermined period of time, determined in an ad-hoc manner.

This enables the SN node to act as a capacitance as mentioned above, thus capable of storing photo-generated electrons that will be transferred in the transfer phase.

Successively to the reset phase, in a transfer phase,
Preferably LEDS are off, but this is not essential,
V_TGtransfer is increased,
S1 switch is kept open.

In the transfer phase, the TG potential is increased to a value comprised between the well potential V_well of the PPD and V_reset.

This way, the photo-generated electrons (e−) filling the PPD well diffuse to the SN through the transfer gate TG.

This charge diffusion causes the potential of the SN to drop from the reset level V_reset to a V_transfer value, said V_transfer value being proportional to the number of transferred charges, that is to the number of photons which reached the PPD.

Preferably, the transfer phase does not last more than a 1 µs.

Successively to the transfer phase, in a readout phase:
V_TGtransfer is set to its low voltage of the integration phase,
S1 switch is kept open.

The value of the voltage at the sense node is proportional to the number of electrons sunk from the PPD, that is to say the number of photon which reached the PPD.

A second embodiment relates to a dual transfer gates pixel arrangement.

Further to the first embodiment, it is proposed here a pixel arrangement where, instead of having the PPD electronically connected to the TGtransfer transistor and the ground like in the previous embodiment, at each pixel level, the PPD is electronically connected between the TGtransfer transistor and another transistor, called TGsink transistor, that is to say two transfer gates TGt and TGs corresponding to TGtransfer transistor and TGsink transistor respectively. This is illustrated in FIG. 4A, which differs from FIG. 2A in that the PPD is additionally connected to a drain voltage $V_{DD}$, which permits emptying the "well" of the PPD independently of the TGtransfer transistor. The exact geometric relationship between TGtransfer and TGsink to the p+zone of the PPD is unimportant, provided that they can both empty the well of the PPD and do not negatively influence each other. Each transistor being situated on opposite sides of the p+zone is a good solution.

To this effect, the TGsink transistor works the same way as the TGtransfer transistor works: depending on the value of the voltage V_TGsink applied to the grid of the TGsink transistor, with regard to the value of the voltage V_TGtransfer applied to the grid of the TGtransfer transistor, it is possible to modify the potential barrier surrounding the PPD, meaning transferring electrons from the PPD well through the TGtransfer transistor for sensing or through the TGsink transistor for sinking to $V_{DD}$. Both transistors TGtransfer and TGsink are independent, although both are arranged to be able to sink charge from the PPD.

FIG. 4B illustrates a pixel according to the second embodiment in a cross-section view, which illustrates clearly how the TGsink transistor is formed immediately adjacent to the p+ doped zone of the PPD in an analogous manner to the TGtransfer transistor, on an opposite side of the PPD to this latter as mentioned above.

In this embodiment, the PPD electrons can be transferred either to one side of the PPD to the Sink Node through the TGsink transistor in a sink phase, or to the Sense Node SN on the other side of the PPD through the TGtransfer transistor in a transfer phase.

FIG. 6 illustrates the different potentials and corresponding transfer of electrons within such a pixel (or macro pixel) in at least one loop of successive phases of operation, from top to bottom of FIG. 6.

In the sink phase:
The LEDs are preferably off,
V_TGsink is set to a high voltage applied to the grid of TGsink transistor,
The drain of TGsink transistor is connected to a constant DC power source, e.g. V_reset (illustrated on FIG. 4A).
V_TG transfer is lower than V_well which is lower than V_TGsink. Accordingly, photo-generated electrons that were within the PPD well cannot go through the TGtransfer transistor and can only go through the TGsink transistor.

Electrons of the PPD well go through the TGsink transistor, e.g. to a constant voltage DC power source. In such a case, because the drain of the TGsink transistor is connected to a constant voltage and not to a capacitor, when proper voltage V_TGsink is applied to the gate of the TGsink transistor, all the electrons of the PPD well are lost.

Accordingly, none of these electrons reaches the acquisition chain (which is located downstream of the Sense Node through the TGtransfer transistor). Accordingly, ambient light does not alter the sensing, the PPD well is emptied.

In the integration phase, similar to the integration phase of the first embodiment:
The LEDs are on, V_TGsink is set to low voltage to close the TGsink transistor and to create a barrier of potential. Preferably V_TGsink is lower than or equal to V_TGtransfer such that no photo-generated electrons can overflow through TGsink transistor, V_TGtransfer is kept at a low voltage.

The potential barrier surrounding the PPD is kept lower than the well potential $V_{well}$ of the PPD. Accordingly the PPD generates photo-generated electrons, which are kept within the PPD well.

However, most of the integrated signal contains a DC component. Transferring a small fraction of the signal exceeding a predetermined threshold (offset) enables the readout performed after the sense node to subtract said offset from said DC component.

In the reset phase:

Preferably LEDS are off,

V_SN is set to V_reset.

This way, the voltage of the sense node SN is increased and set to V_reset value, draining all electrons (if any) within the SN well to the V_reset DC power source, but photo-generated electrons are still kept within the PPD well during the reset phase.

Then the reset switch S1 is opened for a predetermined period of time, as required.

This enables the SN node to act as a capacitance, thus capable of storing photo-generated electrons that will be transferred in the transfer phase.

In the transfer phase,

The LEDs are preferably off to save power,

TGsink potential (TGs) is maintained,

TGtransfer (TGt) potential is increased to a value comprised between the well potential V_well of the PPD and V_TGsink.

This way, the photo-generated electrons (e−) filling the PPD well diffuse to the SN through the transfer gate TGt of the TGtransfer transistor, setting the sense node SN to a V_transfer voltage value.

The difference between V_well and V_TGtransfer is the offset (or V_offset) which corresponds to the DC component which is removed from the signal at the pixel level. It should be noted that the minimum value of V_offset can be zero, although it is typically a larger value.

In the readout phase,

The LEDs are preferably off, again to save power.

Photo-generated electrons (e−) on the sense node SN side are read; and photo-generated electrons within the PPD are kept within its potential well.

After the readout of the sense node voltage, the latter can be reset again and a new loop starting from the sink phase can be implemented.

The n layer of a PPD device is a kind of well: once the well is fully filled, because of the barrier of potential on the TGsink transistor side, the additional photo-generated electrons overflow to the SN depletion through the TGtransfer transistor.

Thanks to the V_TGtransfer dynamic value, only the photo-generated electrons overflowing the offset to the SN depletion will be read, and if the V_TGtransfer is set appropriately, this results in only the AC component of the signal (see FIG. 1) being transferred out, leaving the DC component in the well of the PPD, as will be explained in more detail below. In this manner, the signal-to-noise ratio is massively improved, simply by setting V_TGtransfer appropriately, without any signal processing circuitry being situated downstream and consuming power.

The barrier of potential level chosen depends on the ambient light and the AC/DC ratio of the PPG signal in a calibration phase, as will be made clear below.

Typically, this calibration phase comprises setting the V_TGtransfer to a predetermined value then checking if the corresponding pixel is saturated. If the pixel response is saturated, then a loop comprising increasing said predetermined value of V_TGtransfer by a predetermined pitch (i.e. amount) is performed until the pixel response is no longer saturated.

For instance, the calibration phase enables a same device to be used on different users having different skin pigmentations.

After a calibration phase, it is possible to set a predetermined offset level, corresponding to a predetermined amount of the DC which does not overflow through the TGtransfer transistor, by setting a corresponding predetermined value to V_TGtransfer.

For instance, in the calibration phase it is possible to measure the grand total comprising the DC component+the AC component of the signal. It is known that the AC component represents a few percent of such signal. Accordingly, it is possible to set V_TGtransfer such that the predetermined offset level equals 90% of the signal. Reducing the offset by 90% DC enhances the AC/DC ratio by one order of magnitude, leading to less strict dynamic range constraints at the input. In fact, it should be noted that in PPG measurement, PPG signal typically has a very high DC/AC ratio of 20 to e.g. 500, which is not addressable with classical image sensing solutions.

This embodiment further reduces the DC component of the PPD signal; it thus behaves as a DC remover or as a DR enhancer. This comes without extra cost on power and circuit complexity. Such system does this at the earliest stage of the read-out chain without any additional circuitry.

Advantageously, V_TGtransfer is part of an analog device. Accordingly, it is possible to adjust precisely the level of the potential barrier, i.e. the level of the electrons remaining in the PPD vs. the number of the exceeding electrons being transferred to the sense node (overflow). Such adaptation of the potential barrier level can be done in real time.

Adjusting the value of V_TGtransfer enables adjusting the value of a predetermined part of the DC which is not sensed, which in turn, enables avoiding saturation of the sensor, leading to a better signal to noise ratio.

When the value of V_TGsink equals the value of V_TGtransfer, electrons can be integrated within the PPD well; or electrons can be read from the SN.

When the value of V_TGsink is greater than the value of V_TGtransfer, electrons do sink from the PPD through the TGsink transistor when the PPD is not being read.

When the value of V_TGsink is smaller than the value of V_TGtransfer, electrons cannot sink from the PPD through the TGsink transistor while being read through the TGtransfer transistor.

V_TGsink is a constant value which is selectively applied or not to the grid of the TGsink transistor, thanks e.g. to a switch or to a DSP.

Accordingly, the value of V_TGtransfer and of V_TGtransfer only, can be used to control the value of the potential barrier at the edge of the PPD. Such value of V_TGtransfer is set, and can be continuously adapted thanks to a calibration phase, so that the majority of the photogenerated electrons representing the constant component of the PPG signal (offset electrons) are not transferred to the sense node and, instead, remain within the PPD well. Eventually, these electrons can be sunk out in a next phase.

It should be underlined at this stage that, although PPD's are known in image sensors (charge coupled device, CCD's), they are not exploited in the same way as in the present invention. In an image sensor, the aim is to capture and exploit the entirety of the impinging light, since the entire amount of this light contains critical information regarding light intensity. The intensity recorded by each PPD of an image sensor is then used to create the image. As a result, in an image sensor, the entire charge stored in the PPD's charge well is transferred to the remainder of the circuit for signal processing. In the specific case of a PPG sensor, the majority of the light received is simply DC noise, hiding the signal. As described above, some of this comes from ambient light, and some from non-varying reflection from tissue, arteries and veins, the desired signal being simply the varying AC component on top of this noise. When using a conventional PN or PIN photodiode, there is no way to remove this at the level of the photodiode itself, and the entire current generated in the conventional diode must be processed. By exploiting the properties of PPD diodes as described above, it is possible to reject most, if not all, of this DC noise at the level of the PPD, only transferring the small portion of the received light that corresponds to the desired AC component.

A number of the PPD arrangements of FIGS. 4A and 4B can be coupled together to form a so-called "macropixel", as illustrated in FIGS. 5A and 5B. FIG. 5A in particular illustrates a pair of PPD's arranged as in FIGS. 4A and 4B arranged in parallel, and sharing a common drain $V_{DD}$ on the sink side thereof, connected to the PPD via respective sink transistors TGsink. The outputs of the transfer transistors TGtransfer are connected to a common sense node SN, with the PPD's of the micropixel transferring their charges simultaneously to sense node SN (unlike in a classical CIS/CCD/SPAD, in which pixels do not typically share the same sense node. Note that in some CIS a few pixels may share the same sense node for optimizing the fill factor of pixels but they don't transfer their charges at same time to the shared sense node but rather transfer consecutively in a rolling mode). A source follower SF takes its input from the sink node SN, and outputs to further circuitry (see below). All the control lines for controlling the transfer transistors TGtransfer are connected together, likewise the control lines for controlling the sink transistors TGsink. FIG. 5B illustrates this schematically, as a function of the inputs ($V_{DD}$, V_TGsink, V_TGtransfer, Reset and V_reset), and the output downstream of the source follower SF. It should be noted that within the meaning of the invention, the "macropixel" is considered a "pixel" having multiple PPD's and a common sense node.

Although two PPD's are arranged in parallel in FIG. 5, in principle any number can be incorporated, and the image sensing area of the completed PPG device may comprise one or more of these micropixel structures, arranged in parallel and each having its own sense node SN and corresponding output.

The macropixel structure is optimized for the specific properties of a PPG signal which is completely different from the properties of the signal sensed in a classical image sensing. Fundamentally, a PPG output is a one-dimensional signal, and does not require any information regarding the spatial relationship between the individual PPD's, which is mandatory in conventional imaging. Furthermore, use of such macropixels would reduce the image resolution significatively in conventional imaging since they cover a larger area, whereas here, since there is no concept of "resolution", multiple PPD's can be used in parallel to increase the amount of charge available for sampling at extremely short illumination and sampling times.

The reset voltage, the V_well of the PPD device and the transfer gate voltage used during the transfer are all chosen specifically in order to:
   allow the PPDs of the same macropixel to inject the charge in the common sense node SN of the macropixel without cross talk (the PPDs remain independent from each other during the transfer)
   Prevent a predetermined amount of signal from being transferred to the sense node thanks to VTG_transfer level as explained above. The said signal depends on the perfusion index (AC/DC ratio)

The choice of the number of PPDs per macropixel is defined to optimize the signal to noise ratio specifically for the PPG signal characteristics which is a function involving the electronic read noise, photon shot noise, PPDs dark current noise, quantization noise, saturation level, AC/DC ratio or perfusion index, the number of pixels macropixel, the number of macro pixels per array.

Such a function is specific to the PPG signal processing and is not a consideration in image sensor design, as discussed above.

Array of Pixels

Regardless of whether the first or the second embodiment of pixels, or the macropixel structure described above is used, it is advantageous to use a photo detector comprising a plurality of pixels, especially an array of pixels, each pixel comprising one PPD one macropixel.

This leads to significant improvements. Indeed, it has been shown that PPD based imagers achieve outstanding sensitivity and noise performance.

The PPG device proposed in this embodiment bases its functionalities on the distribution of the input light on an array of PPD based pixels and averaging their outputs, this reducing significantly the read-out noise, photonic shot noise and spurious signals.

As mentioned earlier, most of the power consumption of a PPG device is spent in the LEDs emission. The better sensitivity allowed by the proposed device enables to significantly reduce the duty cycle and the illumination of the LEDs, significantly reducing the average bias current and the power consumption.

In addition to this, this new PPG device can also be fully integrated into a single chip, a SOC, which represents a breakthrough with respect to the state-of-the-art-solutions, mostly showing SOBs (discrete electronics).

Replacing a single PD or PIN diode by an array of pixels results at least in the distribution of the input light on the pixels which reduces the dynamic range constraint on the read-out chain. In addition, the averaging of the array pixels output allows a reduction of the read noise variance, which is proportional to the number of averaged outputs.

The fact that there is a reader circuitry at each pixel generates electronic read noise. Averaging the value of all pixels reduces the read noise by a number which is a factor of the total number of pixels of the array. This enables to eradicate the read noise.

The averaging of the outputs of the array pixels is performed in the charge domain. FIG. 11 shows how the output of each pixel is connected to a capacitor C. Although these pixels are illustrated as being those of FIGS. 4A and 4B, they may equally be those of FIGS. 2A and 2B, or macropixels as in FIG. 5A. One possible scheme is shown in FIG. 9C.

The timing diagram related to this schematic (FIG. 9C) is shown in FIG. 8D, in which a "high" signal indicates that a switch (which may e.g. be a FET) is closed. The first sample out of each pixel is stored in capacitors C by opening switches S2 and S3 and closing switches S1. Then, switches S1 are opened and switches S2 are closed to store the second sample in the same way in the corresponding capacitors C. The averaging of the two stored samples is performed by closing switches S3. In this way all the output capacitors related to the same sample (i.e. those downstream of S1 and those downstream of S2 respectively) share their charge resulting into a voltage equal to the average of the array pixels output samples, since the capacitors C have substantially the same capacitance (which applies equally in each embodiment in which they appear). In addition the large capacitance resulting from the parallel connection of a plurality of pixel output capacitors results in a much bigger capacitance acting as a voltage buffer for the following stages e.g. amplifier as shown in FIG. 9C, situated downstream of the capacitors C. This process allows the averaging, multiple sampling and buffering at almost zero power consumption. Thanks to the buffering effect allowed by the parallel capacitors C, a switch capacitor amplifier can be directly implemented as a next stage to amplify the signal with a ratio of C1/C2 and ensure the differentiation of the two samples. Indeed, the switch S4 is first opened with the SAZ switch to store the first sampled and averaged value in capacitor C1. Then, SAZ is closed in order to transfer the charge stored in C1 to C2 and put the amplifier in a mode in which the output points at the amplified difference between the sample stored in C1 and the current voltage at the input. Then S5 is closed to have at the output of the amplifier the amplified difference between the two averaged values sampled on capacitors C. This scheme is totally different from state of the art image sensors which implement active circuitry for pixel data processing which comes at a much higher power cost.

In the array structure presented in different variants in FIGS. 9A 9B and 9C, we perform the readout for the whole array at once. In conventional image sensors (CIS/CCD/SPAD) a readout per photosite in burst/rolling mode is needed. The array in our case is readout as a whole and provides the array average at the same time. In addition, the macropixels' TGtransfer gates allow the cancellation of a defined DC part as described above. In state of the art PPG sensors, this requires complex circuitry.

The array structure allows pulse capturing, ambient light cancellation, noise reduction, DC cancellation with respect to a given perfusion index in less than 10 us for a full array of more than 100,000 PPDs and allows a power consumption at least two orders of magnitude below that achieved by a conventional array. This demonstrates the substantial difference between a pixel array and a conventional image sensor.

Multiple Sampling

The purpose here is to further improve the signal-to-noise ratio SNR.

In a first step, the LEDs are off. Ambient light is sampled for a predetermined length of time thanks to a first capacitor. The signal which is read and recorded only corresponds to ambient light.

In a second step, the LEDs are on for a predetermined length of time, ideally the same as the predetermined length of time for which ambient light is sampled. The light from the ambient light and from the LED is sampled thanks to a second capacitor. The signal which is read and recorded corresponds to LEDs light and ambient light.

This operation is an intrinsic subtraction which eliminates both the constant reset level and also reduces the flicker noise, which is called "Correlated-Double-Sampling" (CDS), using corresponding CDS block or stage.

It is then possible to subtract the signal of the first step from the signal of the second step to get a signal which only corresponds to LEDs light by subtracting the value from the first capacitor from the value of the second capacitor.

The two CDS can be operated within 20 μs (pulse of LED light of 10 μs), it is assumed that ambient light does not change in a significant way within that period of time. This removes any artefacts that don't change within that period of time, e.g. motion artefacts.

It has been previously discussed that the reading-out action is performed in several steps, starting from the reset level sensing and finishing with the CDS.

This mechanism can be enhanced for PPG applications to perform ambient light subtraction and output averaging, i.e. filtering, in an almost fully passive manner, which means inherently zero power.

FIG. 9A an 9B show an elementary column level read-out chain, embedding two CDS stages, CDS1 and CDS2 respectively, each one based on the "inversion-polarity" principle. In each case, the pixels have been shown as those of FIGS. 4A and 4B, but they can likewise be the pixel of FIGS. 2A and 2B, or the macropixels of FIG. 5A.

With reference to FIG. 7A, 9A, 9B and FIG. 8A, the readout operation involves two phases:
first, the extraction of the voltage V_amb associated with the ambient light and,
second, the extraction of the voltage related to the ambient light+LED light.

In the first phase ("Ambient Light" with reference to FIG. 8A) where the LEDs are off, the sense node is first reset by switching the Reset phase. V_reset voltage is then sensed and then stored in a capacitance $C_{SH1}$ (block CDS1 on FIGS. 9A and 9B) by closing switch SH1 and opening switches SH2 and SH3. As a result, the integrated charge associated with the ambient light is stored in a capacitance $C_{SH2}$ (block CDS1 on FIGS. 9A and 9B), by closing switches SH1 and SH3, and opening switches SH2. This stored voltage corresponds to the voltage V_amb of the ambient light+V_reset. Capacitances CSH1 and CSH2 are of substantially the same capacitance, which applies equally to each embodiment in which they appear. It should be noted that when the voltage is indicated as being high on the timing diagrams of the present application, the corresponding switch is closed and current can flow.

Subsequently, switches SH1 and SH2 are opened, and switches SH3 are closed, resulting in both capacitors CHS1 and CSH2 being connected in parallel, with the polarity inverted. In other words, the pole of the capacitor CSH2 into which the charge from the PPD flowed is connected to ground, its other pole, which had previously been grounded by the lower of the two SH2 switches, being connected to the input pole of capacitor CSH 1. Thanks to the inversion potential principle, at the end of the first CDS1 stage, the corresponding voltage level results to be 0.5($V\_C_{SH1}$−$V\_C_{SH2}$), which equals to 0.5(V_amb+V_reset−V_reset) =0.5V_amb. This removes any artefact from a preceding reset. Such result is stored in a CSH4 capacitance (block CDS2 on FIG. 9A), by opening switches SH4 and SH6, while closing switches SH5 to cause charge to flow into capacitor CSH4. Again, it should be noted that capacitors CSH3 and CSH4 have substantially the same capacitance, which applies equally to each embodiment in which they appear.

In a second phase ("LED Light" with reference to FIG. 8A), the LEDs are on, which means that the integrated photoelectrons will result from both the LED and the ambient light which is always present.

In this case, at the end of the first CDS1 stage, similarly to the first phase, the corresponding voltage level results to be approximately equal to: 0.5(V_LED+V_amb+V_reset−V_reset)=0.5(V_LED+V_amb).

As for the first phase, V_LED+V_amb is stored in a capacitance CSH3 (block CDS2 on FIGS. 9A and 9B), right at the end of the second phase.

Since the PPG information of interest is contained in $V_{LED}$ only, the signal can be "cleaned" of ambient light to improve the signal-to-noise ratio.

By construction of block CDS2, it is possible to differentiate $C_{SH4}$ with $C_{SH3}$, then to subtract the voltage 0.5 (V_amb) related to the ambient light from the voltage 0.5(V_amb+V_LED) related to the ambient light+the signal resulting from LED illumination, thus to obtain the voltage 0.25(V_LED) related to the LEDs only, by operating the various switches of the block CDS2 as described above in the context of CDS1, mutatis mutandis. This final signal is then passed to the ADC and converted to a digital signal.

As a result, the signal to noise ratio can be massively improved by subtracting the DC voltage component from the PPD output which corresponds to the received ambient light measured with the LED off can easily be subtracted from the total signal measured with the LED on.

One other embodiment and operation of the presented photoplethysmography (PPG) sensing device allowing ambient light cancellation with one single CDS is described using FIG. 8B and FIG. 7B. Cancelling the ambient light with the scheme as shown in FIG. 8B has the advantage of reducing the number of CDS stages needed.

This ambient light cancellation with one CDS is described as follows based on FIGS. 8B and 7B, in respect of each pixel (or macropixel, if used):
  Resetting the pixel's SN by means of its reset gate.
  Setting the grid of the transfer gate transistor TGtransfer at a low voltage to prevent the charge transfer from the PPDs to the SN
  with the LED off, integrating in the PPD a charge which hence corresponds to ambient light.
  Performing a first transfer to the SN by applying a pulse of higher voltage to the grid of the transfer gate transistor TGtransfer, and storing the resulting output voltage corresponding to V_amb+V_reset in capacitor C_SH1 by opening switches SH2 and SH3, and closing switch SH1.
  Performing a LED pulse and integrating in the PPDs a charge corresponding to ambient and LED light level.
  Performing a second transfer to the SN by applying a pulse of higher voltage to the transfer gate transistor TGtransfer, and storing the resulting output voltage corresponding to V_LED+V_amb+V_reset in capacitor CSH2, by opening switches SH1 and SH3 and closing switches SH2.
  Subtracting the first stored voltage from the second by means of opening the switches SH1 and SH2 and closing the switch SH3 to obtain a voltage corresponding to 0.5(V_LED) which results in the signal generated by receiving LED light, free of ambient light, artefacts, offset, low frequency and ambient noise.

One other embodiment and method operation of the presented photoplethysmography (PPG) sensing device allowing sensing the derivative of the PPG signal instead of the PPG signal itself is described using FIG. 8C and FIG. 7B. Sensing the PPG signal derivative has the advantage of cancelling not only the noise, offset, artefact and spurious signals originating from the readout chain but the ones originating from the LEDs, motion artefacts and the sensor environment as well. Indeed, all these elements corrupting the input signal have a period larger than a few microseconds. Hence sensing the derivative allows the cancellation of all these elements. In conventional PPG sensors, it is not obvious to take to consecutive PPG samples in such a short time, otherwise a larger power consumption for faster circuitry is needed.

The PPG derivative sensing is described as follows based on FIG. 8C and FIG. 7B, for one or mode pixels (or macropixels):
  Resetting the pixel's SN by means of its reset gate,
  Setting the grid of the transfer gate transistor TGtransfer at a low voltage to prevent the charge transfer from the PPD to the SN
  Performing a first LED pulse and integrating in the PPDs a charge corresponding to ambient and LED light.
  Performing a first transfer to the SN by applying a pulse of higher voltage to the TG, and storing the resulting output voltage corresponding to V_LED1+V_amb+V_reset in $C_{SH1}$ in the same manner as described above.
  Performing a second LED pulse and integrating in the PPDs a charge corresponding to ambient and second LED light level. This second LED pulse typically occurs several tens of microseconds after the first, but this can be adapted as desired.
  Performing a second transfer to the SN by applying a pulse of higher voltage to the grid of the transfer gate transistor TGtransfer, and storing the resulting output voltage corresponding to V_LED2+V_amb+V_reset in CSH2 in the same manner as described above.
  Subtracting the first stored voltage from the second by means of closing the switches SH3 as described above to obtain a voltage corresponding to 0.5(V_LED1−V_LED2) which, since V_LED2 was obtained a certain time after V_LED1, results in the derivative of the LED-originated signal free of ambient light, artefacts, offset, low frequency and ambient noise.

This technique has also the advantage of computing the PPG signal derivative with one single readout scheme and one analog to digital conversion.

Multiple Sampling+Array of Pixels

The multiple sampling described here above can be performed simultaneously for all the pixels in a same column, as shown on FIG. 11 which illustrates an array of pixels distributed in an array (m, n) of m column and n lines.

In a same column, pixels share the same sense node SN connected to one voltage buffer, as shown in FIG. 5A.

The inversion polarity principle of FIGS. 7A-7B can be complemented with an averaging of each column among all the columns.

The averaging all the column reduces the read noise variance by a factor equal to the number of columns, this leading to low-noise, low-power performances.

In a first embodiment, FIG. 9A, the two CDS stages illustrated on FIG. 7A take place after the averaging. With respect to FIG. 9A, the sense nodes are first reset to a voltage higher than the pin voltage of the PPDs. The reset level voltage V_reset plus the ambient light voltage V_amb is then read-out and sampled at the output of each voltage buffer. The reset voltages plus the ambient light voltage V_amb are then averaged.

The averaging involves a fully passive circuit made of switches and sampling capacitances, as shown on FIGS. 9A and 9B, and simply involves connecting the capacitors in parallel conventionally. Accordingly, the mere design of the electronic circuit can first perform a double CDS chain and then averages the results, or, on the contrary, first averages the output of each column and after performs the two CDS stages.

As shown in FIG. 11, all the pixels of the array are operated and read-out simultaneously. In FIG. 11, the averaging is performed by sampling the column-level voltages at identical capacitors and connecting them all together.

After this reset operation, the TGtransfer transistor is turned off and the LED is pulsed on for a predetermined period of time to let the integrated charge cumulate in the PPD and overflow to the sense node. The overflowing charge changes linearly the value of the sense node SN voltage.

The outputs of each voltage follower, SFx with respect to FIG. 11 where x is the number of the column, are again averaged at the array output. The successive two CDS stages extract the LED signal voltage, V_LED, getting rid of both the ambient voltage V_amb and the reset voltage V_reset.

In a further embodiment, FIG. 9B, the two CDS stages illustrated on FIG. 7A take place before the averaging. On the contrary to the previous embodiment, in FIG. 9B the reset voltage V_reset plus the ambient light voltage V_amb are first extracted separately for each column. Then the electrons photo-generated from the LED overflow into the sense capacitance and are stored into a dedicated capacitance, one capacitance per column.

The two CDS stages perform independently, per each column, the ambient and reset voltage compensation and only in the end the LED signal voltages are averaged among the m-columns.

In a further embodiment illustrated in FIG. 9C, two CDS stages as in FIG. 7B are reduced into one single CDS. As illustrated on FIGS. 8B, two independent samples will be averaged at the array output: one accounting for the reset voltage V_reset plus the ambient light voltage V_amb and the second for the reset voltage V_reset plus the ambient light voltage V_amb plus V_LED. Referring to FIG. 8D, the successive electronic circuitry extracts the LED signal voltage, V_LED, eliminating both the ambient voltage V_amb and the reset voltage V_reset from the signal in a simple fashion.

The process of averaging and a system level representation is depicted in FIG. 10.

As far as the input noise (in $e^-_{rms}$) is concerned, the shot noise is a limiting factor. Indeed, for a 28.5 dB SNR, accounting for the shot noise only, the shot noise accounts for more than 10 $ke^-_{rms}$ in terms of input referred noise. This means that the solutions of FIGS. 9A-9C may be a good trade-off since they come with both less area and power at the cost of larger noise, since the latter is anyway negligible compared to the shot noise.

This operation is an intrinsic subtraction which eliminates both the constant reset level and also reduces the flicker noise and spurious signals.

Thanks to the present invention, it is possible to remove the DC component of a signal at the pixel level.

The PPD acts as a capacitor whose capacitance value is known. The amount of charges in the PPD can then be calculated by multiplying said capacitance value by V_TGtransfer.

The PPD based image sensor according to the present invention can be a CMOS imager, which is advantageously used in a PPG application. As explained later, a CMOS image sensor can be driven to solve the issues of LED power consumption, dynamic range limitations of a PPG signal which make the signal processing and filtering difficult otherwise.

The device according to the present invention is advantageously built as a system-on-chip (SOC), integrating a different photonic sensing technology with low-noise and low-power signal processing chain, this allowing higher sensitivity, reliable vital parameters measurement at lower active light (LEDs) levels and at the same time fabricated in a standard CMOS process.

As can be seen from the foregoing, with respect to conventional PPG sensing devices, the PPG sensor of the invention has the advantage of complete decoupling between the photoelectrons light integration in the pixel array and the next stages of the readout chain e.g. amplification and analog to digital conversion. This special feature is enabled thanks to the fact that the capacitors can hold an analog value without any external driving trigger. This allows switching-on the power supply to the array only during the light integration time which is typically less than 10 us and switching-off that supply during the rest of readout operation. In this way the overall power consumption of the PPG sensor is even more reduced.

The invention claimed is:

1. A photoplethysmography (PPG) sensing device, the device comprising:
    a pulsed light source,
    at least one pixel for light-to-charge conversion to create photo-generated electrons, comprising:
       a pinned photodiode including a well,
       a sense node, and
       a transfer gate having its source electronically connected to one electronic connection node of the pinned photodiode, and being configured to act as a transfer gate between the pinned photodiode and the sense node to transfer at least part of any integrated photo-generated electrons to the sense node for a read-out, with a grid of the transfer gate being connected to a DC power source.

2. The device of claim 1, comprising a plurality of said pixels, wherein said pixels are disposed as an array.

3. The device of claim 2, further comprising a processor configured to average spatially outputs of the pixels.

4. The device of claim 1, further comprising a first capacitance to store a first value of the output signal of the device, when the pulsed light source is on during a first pulse and the sense node has been allowed to integrate for a predetermined time period, and a second capacitance to store a second value of the output signal of the device when the pulsed light source is on during a second pulse, and the sense node has been allowed to integrate for a predetermined time period, and an analog to digital converter to digitize a difference between the value stored by the first capacitance and the value stored by second capacitance.

5. The device of claim 1, further comprising a first capacitance to store a value of the output signal of the device when the pulsed light source is off and the sense node well has been allowed to integrate for a predetermined time period, and a second capacitance to store a value of the output signal of the device when the pulsed light source is on, and the sense node well has been allowed to integrate for a predetermined time period, and an analog to digital converter to digitize a difference between the value stored by the first capacitance and the value stored by second capacitance.

6. A photoplethysmography (PPG) sensing device, the device comprising:
a pulsed light source,
at least one pixel for light-to-charge conversion to create photo-generated electrons, comprising:
a pinned photodiode including a well,
a sense node, and
a transfer gate having its source electronically connected to one electronic connection node of the pinned photodiode, and being configured to act as a transfer gate between the pinned photodiode and the sense node to transfer at least part of any integrated photo-generated electrons to the sense node for a read-out;
wherein each pixel further comprises a sink gate electronically connected to said pinned photodiode, and being configured to allow photo-generated electrons to sink towards a constant DC power source or a capacitance when the light source is pulsed-off and the photo-generated electrons integration when the light source is pulsed-on.

7. The device of claim 6, further comprising a DC power source connected to a grid of the transfer gate.

8. A photoplethysmography (PPG) sensing device, the device comprising:
a pulsed light source,
at least one pixel for light-to-charge conversion to create photo-generated electrons, comprising:
a pinned photodiode including a well,
a sense node, and
a transfer gate having its source electronically connected to one electronic connection node of the pinned photodiode, and being configured to act as a transfer gate between the pinned photodiode and the sense node to transfer at least part of any integrated photo-generated electrons to the sense node for a read-out;
wherein each of the pixels comprises at least one further pinned photodiode, arranged in parallel with the pinned photodiode and connected to the sense node by means of a respective transfer gate, each of the transfer gates are configured to be operated synchronously.

9. A photoplethysmography (PPG) sensing device, the device comprising:
a pulsed light source,
at least one pixel for light-to-charge conversion to create photo-generated electrons, comprising:
a pinned photodiode including a well,
a sense node, and
a transfer gate having its source electronically connected to one electronic connection node of the pinned photodiode, and being configured to act as a transfer gate between the pinned photodiode and the sense node to transfer at least part of any integrated photo-generated electrons to the sense node for a read-out;
a first capacitance to store a value of an output signal, when the pulsed light source is off and the sense node well is empty, and a second capacitance to store a value of the output signal, when the pulsed light source is off, and the device is just subject to ambient light, and to store a value of the output signal when the pulsed light source is on.

10. The device of claim 9, further comprising: a third capacitance to store a difference between a value stored by the first capacitance and a value stored by the second capacitance, and a fourth capacitance to store a value of the output signal of the device when the pulsed light source is on, an analog to digital converter to digitize a difference between the value stored by the fourth capacitance and the value stored by third capacitance.

11. A method of operating a photoplethysmography (PPG) sensing device, comprising:
pulsing a light source;
detecting light from the light source with a pinned photodiode for light-to-charge conversion to create photo-generated electrons;
in a transfer phase, setting a voltage of a transfer gate transistor to a value between a well potential of the pinned photodiode and a voltage applied to a sink transistor to allow only photo-generated electrons exceeding an offset to be transferred to a sense node for read-out.

12. The method according to claim 11 wherein the voltage of the transfer gate transistor is dynamically adapted.

13. The method according to claim 11, comprising a calibration step comprising:
setting a value of a DC power source to a predetermined value, checking if the corresponding a pixel response exceeds a predetermined threshold value, and
if the pixel response exceeds the threshold value, repeating steps of setting and checking until the corresponding pixel response is no longer exceeding the threshold.

14. The method according to claim 11, comprising:
pulsing-off the light source, and
integrating charge in the pinned photodiode during a predetermined period of time;
transferring the charge to the sense node and storing the charge in a first capacitor so as to generate a voltage corresponding to ambient light;
pulsing-on the light source for at least said predetermined period of time, integrating charge in the pinned photodiode during said predetermined period of time;
transferring the charge to the sense node and storing the charge in a second capacitor so as to generate a voltage corresponding to ambient light mixed with the pulsed light source; and
subtracting the voltage corresponding to the ambient light from the voltage corresponding to the pulsing-on of the pulsed light source mixed with the ambient light to result in a voltage corresponding the detected light originating from the pulsed light source exclusively.

15. The method according to claim 11, wherein said photoplethysmography (PPG) sensing device comprises a plurality of pixels, said method further comprising a step of averaging spatially the outputs of each pixel.

16. The method according to claim 15, wherein the averaging of the pixels is performed in a passive switched-capacitor fashion through the connection of a plurality of capacitors leading to an electronic buffer.

* * * * *